(12) United States Patent
Appel et al.

(10) Patent No.: US 6,242,409 B1
(45) Date of Patent: Jun. 5, 2001

(54) COMPOSITION AND METHOD FOR BLEACHING A SUBSTRATE

(75) Inventors: Adrianus Cornelis Maria Appel, Rotterdam; Ronald Hage, Leiden; Gerrit van der Voet, Vlaardingen, all of (NL)

(73) Assignee: Unilever Home & Personal Care USA, Greenwich, CT (US)

( * ) Notice: Subject to any disclaimer, the term of this patent is extended or adjusted under 35 U.S.C. 154(b) by 0 days.

(21) Appl. No.: 09/388,167

(22) Filed: Sep. 1, 1999

(30) Foreign Application Priority Data

| Sep. 1, 1998 | (GB) | ................................. 9819046 |
| Mar. 19, 1999 | (GB) | ................................. 9906474 |
| Apr. 1, 1999 | (GB) | ................................. 9907714 |

(51) Int. Cl.$^7$ .............................. C11D 3/395; C11D 7/54
(52) U.S. Cl. ................... 510/376; 510/303; 510/311; 8/101; 8/111; 252/186.33
(58) Field of Search .................. 510/303, 311, 510/376; 8/101, 111; 252/186.33

(56) References Cited

FOREIGN PATENT DOCUMENTS

| 197 21 886 | 5/1997 | (DE) . |
| 0 040 131 | 4/1981 | (EP) . |
| 909809 * | 4/1999 | (EP) . |
| 034497 | 7/1998 | (JP) . |
| 95/34628 | 12/1995 | (WO) . |
| 96/06154 | 2/1996 | (WO) . |
| 97/07124 | 2/1997 | (WO) . |
| 97/38074 | 10/1997 | (WO) . |
| 97/48710 | 12/1997 | (WO) . |
| 97/48787 | 12/1997 | (WO) . |
| WO 00/12667 * | 3/2000 | (WO) . |
| WO 00/12808 * | 3/2000 | (WO) . |

OTHER PUBLICATIONS

Journal of Surfactants and Detergents, vol., 1, No. 2 (Apr. 1998), "Oxygen Bleaching Systems in Domestic Laundry" by Neal J. Milne, pp. 254–261 (Apr. 1998).

\* cited by examiner

*Primary Examiner*—Gregory DelCotto
(74) *Attorney, Agent, or Firm*—Milton L. Honig

(57) ABSTRACT

The invention relates to catalytically bleaching substrates, especially laundry fabrics, with atmospheric oxygen or air. A method of bleaching a substrate is provided that comprises applying to the substrate, in an aqueous medium, an organic substance which forms a complex with a transition metal, the complex catalysing bleaching of the substrate by atmospheric oxygen. Also provided is a bleaching composition comprising, in an aqueous medium, atmospheric oxygen and an organic substance which forms a complex with a transition metal, the complex catalysing bleaching of the substrate by the atmospheric oxygen, wherein the aqueous medium is substantially devoid of peroxygen bleach or a peroxy-based or -generating bleach system.

6 Claims, No Drawings

COMPOSITION AND METHOD FOR BLEACHING A SUBSTRATE

This invention relates to compositions and methods for catalytically bleaching substrates with atmospheric oxygen.

Peroxygen bleaches are well known for their ability to remove stains from substrates. Traditionally, the substrate is subjected to hydrogen peroxide, or to substances which can generate hydroperoxyl radicals, such as inorganic or organic peroxides. Generally, these systems must be activated. One method of activation is to employ wash temperatures of 60° C. or higher. However, these high temperatures often lead to inefficient cleaning, and can also cause premature damage to the substrate.

A preferred approach to generating hydroperoxyl bleach radicals is the use of inorganic peroxides coupled with organic precursor compounds. These systems are employed for many commercial laundry powders. For example, various European systems are based on tetraacetyl ethylenediamine (TAED) as the organic precursor coupled with sodium perborate or sodium percarbonate, whereas in the United States laundry bleach products are typically based on sodium nonanoyloxybenzenesulphonate (SNOBS) as the organic precursor coupled with sodium perborate.

Precursor systems are generally effective but still exhibit several disadvantages. For example, organic precursors are moderately sophisticated molecules requiring multi-step manufacturing processes resulting in high capital costs. Also, precursor systems have large formulation space requirements so that a significant proportion of a laundry powder must be devoted to the bleach components, leaving less room for other active ingredients and complicating the development of concentrated powders. Moreover, precursor systems do not bleach very efficiently in countries where consumers have wash habits entailing low dosage short wash times, cold temperatures and low wash liquor to substrate ratios.

Alternatively, or additionally, hydrogen peroxide and peroxy systems can be activated by bleach catalysts, such as by complexes of iron and the ligand N4Py (i.e. N, N-bis(pyridin-2-yl-methyl)-bis(pyridin-2-yl)methylamine) disclosed in WO95/34628, or the ligand Tpen (i.e. N, N, N', N'-tetra(pyridin-2-yl-methyl)ethylenediamine) disclosed in WO97/48787. According to these publications, molecular oxygen may be used as the oxidant as an alternative to peroxide generating systems. However, no role in catalysing bleaching by atmospheric oxygen in an aqueous medium is reported.

It has long been thought desirable to be able to use atmospheric oxygen (air) as the source for a bleaching species, as this would avoid the need for costly hydroperoxyl generating systems. Unfortunately, air as such is kinetically inert towards bleaching substrates and exhibits no bleaching ability. Recently some progress has been made in this area. For example, WO 97/38074 reports the use of air for oxidising stains on fabrics by bubbling air through an aqueous solution containing an aldehyde and a radical initiator. A broad range of aliphatic, aromatic and heterocyclic aldehydes is reported to be useful, particularly para-substituted aldehydes such as 4-methyl-, 4-ethyl- and 4-isopropyl benzaldehyde, whereas the range of initiators disclosed includes N-hydroxysuccinimide, various peroxides and transition metal coordination complexes.

However, although this system employs molecular oxygen from the air, the aldehyde component and radical initiators such as peroxides are consumed during the bleaching process. These components must therefore be included in the composition in relatively high amounts so as not to become depleted before completion of the bleaching process in the wash cycle. Moreover, the spent components represent a waste of resources as they can no longer participate in the bleaching process.

Accordingly, it would be desirable to be able to provide a bleaching system based on atmospheric oxygen or air that does not rely primarily on hydrogen peroxide or a hydroperoxyl generating system, and that does not require the presence of organic components such as aldehydes that are consumed in the process. Moreover, it would be desirable to provide such a bleaching system that is effective in aqueous medium.

We have surprisingly found that the long held wish to use atmospheric oxygen or air for bleaching substrates can be fulfilled without the attendant disadvantages referred to above. This has now been achieved by means of an organic substance that catalyses bleaching of the substrate by atmospheric oxygen, using the composition and method in accordance with the present invention.

Accordingly, in a first aspect, the present invention provides a bleaching composition comprising, in an aqueous medium, atmospheric oxygen and an organic substance which forms a complex with a transition metal, the complex catalysing bleaching of a substrate by the atmospheric oxygen, wherein the aqueous medium is substantially devoid of peroxygen bleach or a peroxy-based or -generating bleach system. The medium is therefore preferably insensitive or stable to catalase, which acts on peroxy species.

In a second aspect, the present invention provides a method of bleaching a substrate comprising applying to the substrate, in an aqueous medium, an organic substance which forms a complex with a transition metal, the complex catalysing bleaching of the substrate by atmospheric oxygen.

Furthermore, in a third aspect, the present invention provides the use of an organic substance which forms a complex with a transition metal as a catalytic bleaching agent for a substrate in an aqueous medium substantially devoid of peroxygen bleach or a peroxy-based or -generating bleach system, the complex catalysing bleaching of the substrate by the atmospheric oxygen.

Advantageously, the method according to the present invention permits all or the majority of the bleaching species in the medium (on an equivalent weight basis) to be derived from atmospheric oxygen. Thus, the medium can be made wholly or substantially devoid of peroxygen bleach or a peroxy-based or -generating bleach system. Furthermore, the organic substance is a catalyst for the bleaching process and, as such, is not consumed but can continue to participate in the bleaching process. The catalytically activated bleaching system of the type in accordance with the present invention, which is based on atmospheric oxygen, is therefore both cost-effective and environmentally friendly.

Moreover, the bleaching system is operable under unfavourable wash conditions which include low temperatures, short contact times and low dosage requirements.

Furthermore, the method is effective in an aqueous medium and is therefore particularly applicable to bleaching of laundry fabrics. Therefore, whilst the composition and method according to the present invention may be used for bleaching any suitable substrate, the preferred substrate is a laundry fabric.

The bleaching method may be carried out by simply leaving the substrate in contact with the medium for a sufficient period of time. Preferably, however, the aqueous medium on or containing the substrate is agitated.

The organic substance may comprise a preformed complex of a ligand and a transition metal. Alternatively, the organic substance may comprise a free ligand that complexes with a transition metal already present in the water or that complexes with a transition metal present in the substrate. The organic substance may also be included in the form of a composition of a free ligand or a transition metal-substitutable metal-ligand complex, and a source of transition metal, whereby the complex is formed in situ in the medium.

The organic substance forms a complex with one or more transition metals, in the latter case for example as a dinuclear complex. Suitable transition metals include for example: manganese in oxidation states II–V, iron I–IV, copper I–III, cobalt I–III, nickel I–III, chromium II–VII, silver I–II, titanium II–IV, tungsten IV–VI, palladium II, ruthenium II–V, vanadium II–V and molybdenum II–VI.

In a preferred embodiment, the organic substance forms a complex of the general formula (A1):

$$[M_a L_k X_n] Y_m$$

in which:

M represents a metal selected from Mn(II)-(III)-(IV)-(V), Cu(I)-(II)-(III), Fe(I)-(II)-(III)-(IV), Co(I)-(II)-(III), Ni(I)-(II)-(III), Cr(II)-(III)-(IV)-(V)-(VI)-(VII), Ti(II)-(III)-(IV), V(II)-(III)-(IV)-(V), Mo(II)-(III)-(IV)-(V)-(VI), W(IV)-(V)-(VI), Pd(II), Ru(II)-(III)-(IV)-(V) and Ag(I)-(II), and preferably selected from Mn(II)-(III)-(IV)-(V), Cu(I)-(II), Fe(II)-(III)-(IV) and Co(I)-(II)-(III);

L represents a ligand as herein defined, or its protonated or deprotonated analogue;

X represents a coordinating species selected from any mono, bi or tri charged anions and any neutral molecules able to coordinate the metal in a mono, bi or tridentate manner, preferably selected from $O^{2-}$, $RBO_2^{2-}$, $RCOO^-$, $RCONR^-$, $OH^-$, $NO_3^-$, $NO_2^-$, $NO$, $CO$, $S^{2-}$, $RS^-$, $PO_3^{4-}$, STP-derived anions, $PO_3OR^{3-}$, $H_2O$, $CO_3^{2-}$, $HCO_3^-$, $ROH$, $NRR'R''$, $RCN$, $Cl^-$, $Br^-$, $OCN^-$, $SCN^-$, $CN^-$, $N_3^-$, $F^-$, $I^-$, $RO^-$, $ClO_4^-$, $SO_4^{2-}$, $HSO_4^-$, $SO_3^{2-}$ and $RSO_3^-$, and more preferably selected from $O^{2-}$, $RBO_2^{2-}$, $RCOO^-$, $OH^-$, $NO_3^-$, $NO_2^-$, $NO$, $CO$, $CN^-$, $S^{2-}$, $RS^-$, $PO_3^{4-}$, $H_2O$, $CO_3^{2-}$, $HCO_3^-$, $ROH$, $NRR'R''$, $Cl^-$, $Br^-$, $OCN^-$, $SCN^-$, $RCN$, $N_3^-$, $F^-$, $I^-$, $RO^-$, $ClO_4^-$, $SO_4^{2-}$, $HSO_4^-$, $SO_3^{2-}$ and $RSO_3^-$ (preferably $CF_3SO_3^-$);

Y represents any non-coordinated counter ion, preferably selected from $ClO_4^-$, $BR_4^-$, $[FeCl_4]^-$, $PF_6^-$, $RCOO^-$, $NO_3^-$, $NO_2^-$, $RO^-$, $N^+RR'R''R'''$, $Cl^-$, $Br^-$, $F^-$, $I^-$, $RSO_3^-$, $S_2O_6^{2-}$, $OCN^-$, $SCN^-$, $Li^+$, $Ba^{2+}$, $Na^+$, $Mg^{2+}$, $K^+$, $Ca^{2+}$, $Cs^+$, $PR_4^+$, $RBO_2^{2-}$, $SO_4^{2-}$, $HSO_4^-$, $SO_3^{2-}$, $SbCl_6^-$, $CuCl_4^{2-}$, $CN$, $PO_4^{3-}$, $HPO_4^{2-}$, $H_2PO_4^-$, STP-derived anions, $CO_3^{2-}$, $HCO_3^-$ and $BF_4^-$, and more preferably selected from $ClO_4^-$, $BR_4^-$, $[FeCl_4]^-$, $PF_6^-$, $RCOO^-$, $NO_3^-$, $NO_2^-$, $RO^-$, $N^+RR'R''R'''$, $Cl^-$, $Br^-$, $F^-$, $I^-$, $RSO_3^-$ (preferably $CF_3SO_3^-$), $S_2O_6^{2-}$, $OCN^-$, $SCN^-$, $Li^+$, $Ba^{2+}$, $Na^+$, $Mg^{2+}$, $K^+$, $Ca^{2+}$, $PR_4^+$, $SO_4^{2-}$, $HSO_4^-$, $SO_3^{2-}$, and $BF_4^-$;

R, R', R", R'" independently represent a group selected from hydrogen. hydroxyl, —OR (wherein R=alkyl, alkenyl, cycloalkyl, heterocycloalkyl, aryl, heteroaryl or carbonyl derivative group), —OAr, alkyl, alkenyl, cycloalkyl, heterocycloalkyl, aryl, heteroaryl and carbonyl derivative groups, each of R, Ar, alkyl, alkenyl, cycloalkyl, heterocycloalkyl, aryl, heteroaryl and carbonyl derivative groups being optionally substituted by one or more functional groups E, or R6 together with R7 and independently R8 together with R9 represent oxygen, wherein E is selected from functional groups containing oxygen, sulphur, phosphorus, nitrogen, selenium, halogens, and any electron donating and/or withdrawing groups, and preferably R, R', R", R'" represent hydrogen, optionally substituted alkyl or optionally substituted aryl, more preferably hydrogen or optionally substituted phenyl, naphthyl or $C_{1-4}$-alkyl;

a represents an integer from 1 to 10, preferably from 1 to 4;

k represents an integer from 1 to 10;

n represents zero or an integer from 1 to 10, preferably from 1 to 4;

m represents zero or an integer from 1 to 20, preferably from 1 to 8.

Preferably, the ligand L is of the general formula (BI):

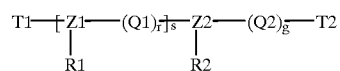

wherein g represents zero or an integer from 1 to 6;

r represents an integer from I to 6;

s represents zero or an integer from 1 to 6;

Z1 and Z2 independently represent a heteroatom or a heterocyclic or heteroaromatic ring, Z1 and/or Z2 being optionally substituted by one or more functional groups E as defined below;

Q1 and Q2 independently represent a group of the formula:

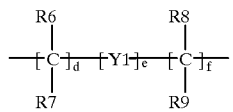

wherein

10>d+e+f>1; d=0–9; e=0–9; f=0–9, each Y1 is independently selected from —O—, —S—, —SO—, —SO$_2$—, —(G$^1$)N—, —(G$^1$)(G$^2$)N— (wherein G$^1$ and G$^2$ are as defined below), —C(O)—, arylene, alkylene, heteroarylene, —P— and —P(O)—;

if s>1, each —[—Z1(R1)—(Q1)$_r$—]— group is independently defined;

R1, R2, R6, R7, R8, R9 independently represent a group selected from hydrogen, hydroxyl, —OR (wherein R=alkyl, alkenyl, cycloalkyl, heterocycloalkyl, aryl, heteroaryl or carbonyl derivative group), —OAr, alkyl, alkenyl, cycloalkyl, heterocycloalkyl, aryl, heteroaryl and carbonyl derivative groups, each of R, Ar, alkyl, alkenyl, cycloalkyl, heterocycloalkyl, aryl, heteroaryl and carbonyl derivative groups being optionally substituted by one or more functional groups E, or R6 together with R7 and independently R8 together with R9 represent oxygen;

E is selected from functional groups containing oxygen, sulphur, phosphorus, nitrogen, selenium, halogens, and any electron donating and/or withdrawing groups (preferably E is selected from hydroxy, mono- or polycarboxylate derivatives, aryl, heteroaryl, sulphonate, thiol (—RSH), thioethers (—R—S—R'), disulphides (—RSSR'), dithiolenes, mono- or polyphosphonates, mono- or polyphosphates, electron donating groups and electron withdrawing groups, and groups of formulae $(G^1)(G^2)N—$, $(G^1)(G^2)(G^3)N—$, $(G^1)(G^2)N—C(O)—$, $G^3O—$ and $G^3C(O)—$, wherein each of $G^1$, $G^2$ and $G^3$ is independently selected from hydrogen, alkyl, electron donating groups and electron withdrawing groups (in addition to any amongst the foregoing));

or one of R1–R9 is a bridging group bound to another moiety of the same general formula;

T1 and T2 independently represent groups R4 and R5, wherein R4 and R5 are as defined for R1–R9, and if g=0 and s>0, R1 together with R4, and/or R2 together with R5, may optionally independently represent =CH—R10, wherein R10 is as defined for R1–R9, or T1 and T2 may together (—T2—T1—) represent a covalent bond linkage when s>1 and g>0;

if Z1 and/or Z2 represent N and T1 and T2 together represent a single bond linkage and R1 and/or R2 are absent, Q1 and/or Q2 may independently represent a group of the forrnula: $=CH—[—Y1—]_e—CH=$, optionally any two or more of R1, R2, R6, R7, R8, R9 independently are linked together by a covalent bond;

if Z1 and/or Z2 represents O, then R1 and/or R2 do not exist;

if Z1 and/or Z2 represents S, N, P, B or Si then R1 and/or R2 may be absent;

if Z1 and/or Z2 represents a heteroatom substituted by a functional group E then R1 and/or R2 and/or R4 and/or R5 may be absent.

The groups Z1 and Z2 preferably independently represent an optionally substituted heteroatom selected from N, P, O, S, B and Si or an optionally substituted heterocyclic ring or an optionally substituted heteroaromatic ring selected from pyridine, pyrimidines, pyrazine, pyramidine, pyrazole, pyrrole, imidazole, benzimidazole, quinoleine, isoquinoline, carbazole, indole, isoindole, furane, thiophene, oxazole and thiazole.

The groups R1–R9 are preferably independently selected from —H, hydroxy-$C_0$–$C_{20}$-alkyl, halo-$C_0$–$C_{20}$-alkyl, nitroso, formyl-$C_0$–$C_{20}$-alkyl, carboxyl-$C_0$–$C_{20}$-alkyl and esters and salts thereof, carbamoyl-$C_0$–$C_{20}$-alkyl, sulpho-$C_0$–$C_{20}$-alkyl and esters and salts thereof, sulphamoyl-$C_0$–$C_{20}$-alkyl, amino-$C_0$–$C_{20}$-alkyl, aryl-$C_0$–$C_{20}$-alkyl, heteroaryl-$C_0$–$C_{20}$-alkyl, $C_0$–$C_{20}$-alkyl, alkoxy-$C_0$–$C_8$-alkyl, carbonyl-$C_0$–$C_6$-alkoxy, and aryl-$C_0$–$C_6$-alkyl and $C_0$–$C_{20}$-alkylamide.

One of R1–R9 may be a bridging group which links the ligand moiety to a second ligand moiety of preferably the same general structure. In this case the bridging group may have the formula —$C_{n'}(R11)(R12)—(D)_p—C_{m'}(R11)(R12)$— bound between the two moieties, wherein p is zero or one, D is selected from a heteroatom or a heteroatom-containing group, or is part of an aromatic or saturated homonuclear and heteronuclear ring, n' is an integer from 1 to 4, m' is an integer from 1 to 4, with the proviso that n'+m'<=4, R11 and R12 are each independently preferably selected from —H, NR13 and OR14, alkyl, aryl, optionally substituted, and R13 and R14 are each independently selected from —H, alkyl, aryl, both optionally substituted. Alternatively, or additionally, two or more of R1–R9 together represent a bridging group linking atoms, preferably hetero atoms, in the same moiety, with the bridging group preferably being alkylene or hydroxy-alkylene or a heteroaryl-containing bridge.

In a first variant according to formula (BI), the groups T1 and T2 together form a single bond linkage and s>1, according to general formula (BII):

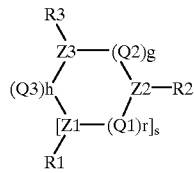

wherein Z3 independently represents a group as defined for Z1 or Z2; R3 independently represents a group as defined for R1–R9; Q3 independently represents a group as defined for Q1, Q2; h represents zero or an integer from 1 to 6; and s'=s–1.

In a first embodiment of the first variant in general formula (BII), s'=1, 2 or 3; r=g=h=1; d=2 or 3; e=f=0; R6=R7=H, preferably such that the ligand has a general formula selected from:

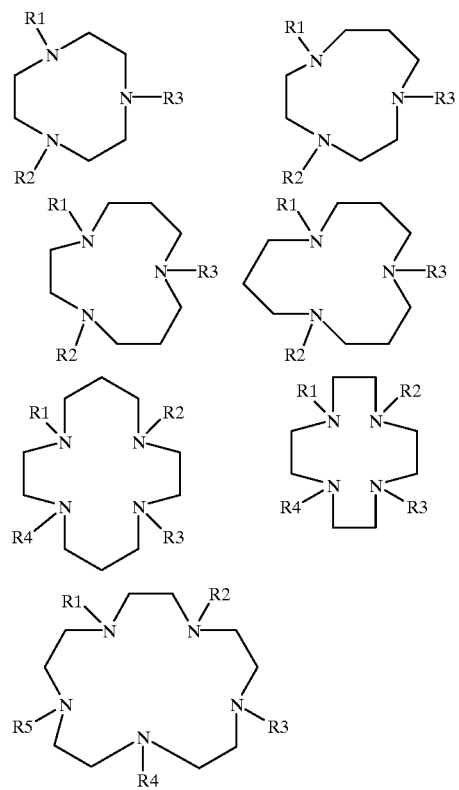

and more preferably selected from:

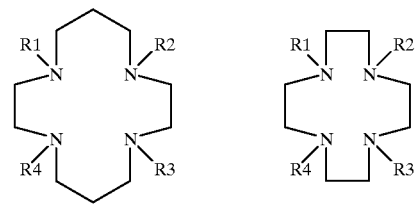

-continued

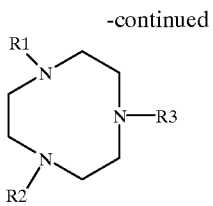

In these preferred examples, R1, R2, R3 and R4 are preferably independently selected from —H, alkyl, aryl, heteroaryl, and/or one of R1–R4 represents a bridging group bound to another moiety of the same general formula and/or two or more of R1–R4 together represent a bridging group linking N atoms in the same moiety, with the bridging group being alkylene or hydroxy-alkylene or a heteroaryl-containing bridge, preferably heteroarylene. More preferably, R1, R2, R3 and R4 are independently selected from —H, methyl, ethyl, isopropyl, nitrogen-containing heteroaryl, or a bridging group bound to another moiety of the same general formula or linking N atoms in the same moiety with the bridging group being alkylene or hydroxy-alkylene.

According to this first embodiment, in the complex $[M_aL_kX_n]Y_m$ preferably:

M=Mn(II)-(IV), Cu(I)-(III), Fe(II)-(III), Co(II)-(III);

X=$CH_3CN$, $OH_2$, $Cl^-$, $Br^-$, $OCN^-$, $N_3^-$, $SCN^-$, $OH^-$, $O^{2-}$, $PO_4^{3-}$, $C_6H_5BO_2^{2-}$, $RCOO^-$;

Y=$ClO_4^-$, $BPh_4^-$, $Br^-$, $Cl^-$, $[FeCl_4]^-$, $PF_6^-$, $NO_3^-$ a=1,2,3,4;

n=0,1,2,3,4,5,6,7,8,9;

m=1,2,3,4; and k=1,2,4.

In a second embodiment of the first variant, in general formula (BII), s'=2; r=g=h=1; d=f=0; e=1; and each Y1 is independently alkylene or heteroarylene. The ligand preferably has the general formula:

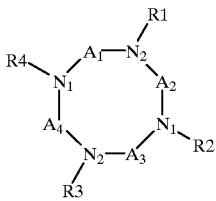

wherein $A_1$, $A_2$, $A_3$, $A_4$ are independently selected from $C_{1-9}$-alkylene or heteroarylene groups; and $N_1$ and $N_2$ independently represent a hetero atom or a heteroarylene group.

In a preferred second embodiment, $N_1$ represents an aliphatic nitrogen, $N_2$ represents a heteroarylene group, R1, R2, R3, R4 each independently represent —H, alkyl, aryl or heteroaryl, and $A_1$, $A_2$, $A_3$, $A_4$ each represent —$CH_2$—.

One of R1–R4 may represent a bridging group bound to another moiety of the same general formula and/or two or more of R1–R4 may together represent a bridging group linking N atoms in the same moiety, with the bridging group being alkylene or hydroxy-alkylene or a heteroaryl-containing bridge. Preferably, R1, R2, R3 and R4 are independently selected from —H, methyl, ethyl, isopropyl, nitrogen-containing heteroaryl, or a bridging group bound to another moiety of the same general formula or linking N atoms in the same moiety with the bridging group being alkylene or hydroxy-alkylene.

Particularly preferably, the ligand has the general formula:

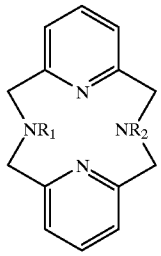

wherein R1, R2 each independently represent —H, alkyl, aryl or heteroaryl.

According to this second embodiment, in the complex $[M_aL_kX_n]Y_m$, preferably:

M=Fe(II)-(III), Mn(II)-(IV), Cu(II), Co(II)-(III);

X=$CH_3CN$, $OH_2$, $Cl^-$, $Br^-$, $OCN^-$, $N_3^-$, $SCN^-$, $OH^-$, $O^{2-}$, $PO_4^{3-}$, $C_6H_5BO_2^{2-}$, $RCOO^-$;

Y=$ClO_4^-$, $BPh_4^-$, $Br^-$, $Cl^-$, $[FeCl_4]^-$, $PF_6^-$, $NO_3^-$;

a=1,2,3,4;

n=0,1,2,3,4,5,6,7,8,9;

m=1,2,3,4; and k=1,2,4.

In a third embodiment of the first variant, in general formula (BII), s'=2 and r=g=h=1, according to the general formula:

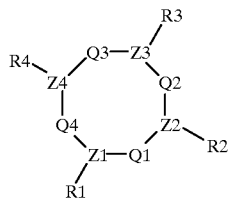

In this third embodiment, preferably each Z1–Z4 represents a heteroaromatic ring; e=f=0; d=1; and R7 is absent, with preferably R1=R2=R3=R4=2,4,6-trimethyl-3-$SO_3Na$-phenyl, 2,6-diCl-3(or 4)-$SO_3Na$-phenyl.

Alternatively, each Z1–Z4 represents N; R1–R4 are absent; both Q1 and Q3 represent =CH—[—Y1—]$_e$—CH=; and both Q2 and Q4 represent —$CH_2$—[—Y1—]$_n$—$CH_2$—.

Thus, preferably the ligand has the general formula:

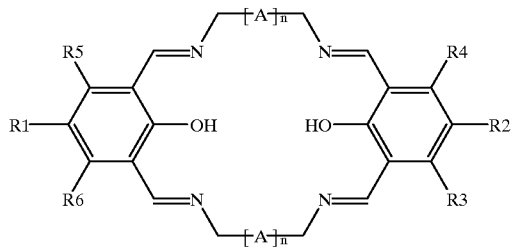

wherein A represents optionally substituted alkylene optionally interrupted by a heteroatom; and n is zero or an integer from 1 to 5.

Preferably, R1–R6 represent hydrogen, n=1 and A=—CH$_2$—, —CHOH—, —CH$_2$N(R)CH$_2$—or —CH$_2$CH$_2$N(R)CH$_2$CH$_2$— wherein R represents hydrogen or alkyl, more preferably A=—CH$_2$—, —CHOH—or —CH$_2$CH$_2$NHCH$_2$CH$_2$—.

According to this third embodiment, in the complex [M$_a$L$_k$X$_n$]Y$_m$ preferably:

M=Mn(II)-(IV), Co(II)-(III), Fe(II)-(III);
X=CH$_3$CN, OH$_2$, Cl$^-$, Br$^-$, OCN$^-$, N$_3^-$, SCN$^-$, OH$^-$, O$^{2-}$, PO$_4^{3-}$, C$_6$H$_5$BO$_2^{2-}$, RCOO$^-$;
Y=ClO$_4^-$, BPh$_4^-$, Br$^-$, Cl$^-$, [FeCl$_4$]$^-$, PF$_6^-$, NO$_3^-$;
a=1,2,3,4;
n=0,1,2,3,4,5,6,7,8,9;
m=1,2,3,4; and
k=1,2,4.

In a second variant according to formula (BI), T1 and T2 independently represent groups R4, R5 as defined for R1–R9, according to the general formula (BIII):

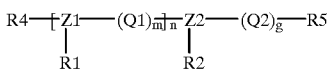

In a first embodiment of the second variant, in general formula (BIII), s=1; r=1; g=0; d=f=1; e=1–4; Y1=—CH$_2$—; and R1 together with R4, and/or R2 together with R5, independently represent =CH—R10, wherein R10 is as defined for R1–R9. In one example, R2 together with R5 represents =CH—R10, with R1 and R4 being two separate groups. Alternatively, both R1 together with R4, and R2 together with R5 may independently represent =CH—R10. Thus, preferred ligands may for example have a structure selected from:

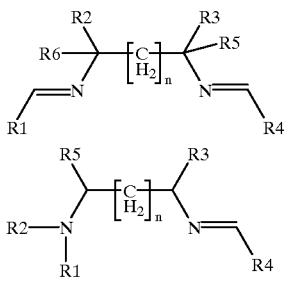

Preferably, the ligand is selected from:

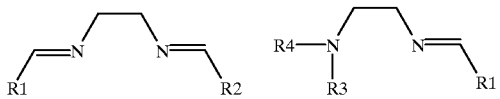

wherein R1 and R2 are selected from optionally substituted phenols, heteroaryl-C$_0$–C$_{20}$-alkyls, R3 and R4 are selected from —H, alkyl, aryl, optionally substituted phenols, heteroaryl-C$_0$–C$_{20}$-alkyls, alkylaryl, aminoalkyl, alkoxy, more preferably R1 and R2 being selected from optionally substituted phenols, heteroaryl-C$_0$–C$_2$-alkyls, R3 and R4 are selected from —H, alkyl, aryl, optionally substituted phenols, nitrogen-heteroaryl-C$_0$–C$_2$-alkyls.

According to this first embodiment, in the complex [M$_a$L$_k$X$_n$]Y$_m$ preferably:

M=Mn(II)-(IV), Co(II)-(III), Fe(II)-(III);
X=CH$_3$CN, OH$_2$, Cl$^-$, Br$^-$, OCN$^-$, N$_3^-$, SCN$^-$, OH$^-$, O$^{2-}$, PO$_4^{3-}$, C$_6$H$_5$BO$_2^{2-}$, RCOO$^-$;
Y=ClO$_4^-$, BPh$_4^-$, Br$^-$, Cl$^-$, [FeCl$_4$]$^-$, PF$_6^-$, NO$_3^-$;
a=1,2,3,4;
n=0,1,2,3,4,5,6,7,8,9;
m=1,2,3,4; and
k=1,2,4.

In a second embodiment of the second variant, in general formula (BIII), s=1; r=1; g=0; d=f=1; e=1–4; Y1=—C(R') (R"), wherein R' and R" are independently as defined for R1–R9. Preferably, the ligand has the general formula:

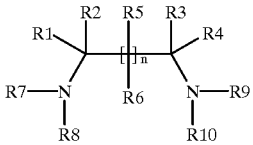

The groups R1, R2, R3, R4, R5 in this formula are preferably —H or C$_0$–C$_{20}$-alkyl, n=0 or 1, R6 is —H, alkyl, —OH or —SH, and R7, R8, R9, R10 are preferably each independently selected from —H, C$_0$–C$_{20}$-alkyl, heteroaryl-C$_0$–C$_{20}$-alkyl, alkoxy-C$_0$–C$_8$-alkyl and amino-C$_0$–C$_{20}$-alkyl.

According to this second embodiment, in the complex [M$_a$L$_k$X$_n$]Y$_m$ preferably:

M=Mn(II)-(IV), Fe(II)-(III), Cu(II), Co(II)-(III);
X=CH$_3$CN, OH$_2$, Cl$^-$, Br$^-$, OCN$^-$, N$_3^-$, SCN$^-$, OH$^-$, O$^{2-}$, PO$_4^{3-}$, C$_6$H$_5$BO$_2^{2-}$, RCOO$^-$;
Y=ClO$_4^-$, BPh4$^-$, Br$^-$, Cl$^-$, [FeCl$_4$]$^-$, PF$_6^-$, NO$_3^-$;
a=1,2,3,4;
n=0,1,2,3,4;
m=0,1,2, 3,4,5,6,7,8; and
k=1,2,3,4.

In a third embodiment of the second variant, in general formula (BIII), s=0; g=1; d=e=0; f=1–4. Preferably, the ligand has the general formula:

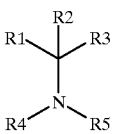

More preferably, the ligand has the general formula:

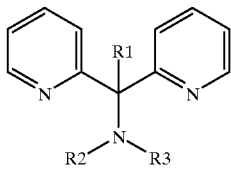

wherein R1, R2, R3 are as defined for R2, R4, R5.

According to this third embodiment, in the complex [M$_a$L$_k$X$_n$]Y$_m$ preferably:

M=Mn(II)-(IV), Fe(II)-(III), Cu(II), Co(II)-(III);
X=CH$_3$CN, OH$_2$, Cl$^-$, Br$^-$, OCN$^-$, N$_3^-$, SCN$^-$, OH$^-$, O$^{2-}$, PO$_4^{3-}$, C$_6$H$_5$BO$_2^{2-}$, RCOO$^-$;
Y=ClO$_4^-$, BPh$_4^-$, Br$^-$, Cl$^-$, [FeCl$_4$]$^-$, PF$_6^-$, NO$_3^-$;
a=1,2,3,4;
n=0,1,2,3,4;

m=0,1,2,3,4,5,6,7,8; and k=1,2,3,4.

In a fourth embodiment of the second variant, the organic substance forms a complex of the general formula (A):

$$[LMX_n]^z Y_q$$

in which

M represents iron in the II, III, IV or V oxidation state, manganese in the II, III, IV, VI or VII oxidation state, copper in the I, II or III oxidation state, cobalt in the II, III or IV oxidation state, or chromium in the II–VI oxidation state;

X represents a coordinating species;

n represents zero or an integer in the range from 0 to 3;

z represents the charge of the complex and is an integer which can be positive, zero or negative;

Y represents a counter ion, the type of which is dependent on the charge of the complex;

q=z/[charge Y]; and

L represents a pentadentate ligand of the general formula (B):

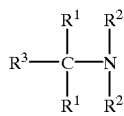

wherein each $R^1$, $R^2$ independently represents —$R^4$—$R^5$, $R^3$ represents hydrogen. optionally substituted alkyl, aryl or arylalkyl, or —$R^4$—$R^5$, each $R^4$ independently represents a single bond or optionally substituted alkylene, alkenylene, oxyalkylene, aminoalkylene. alkylene ether, carboxylic ester or carboxylic amide, and each $R^5$ independently represents an optionally N-substituted aminoalkyl group or an optionally substituted heteroaryl group selected from pyridinyl, pyrazinyl, pyrazolyl, pyrrolyl, imidazolyl, benzimidazolyl, pyrimidinyl, triazolyl and thiazolyl.

The ligand L having the general formula (B), as defined above, is a pentadentate ligand. By 'pentadentate' herein is meant that five hetero atoms can coordinate to the metal M ion in the metal-complex.

In formula (B), one coordinating hetero atom is provided by the nitrogen atom in the methylamine backbone, and preferably one coordinating hetero atom is contained in each of the four $R^1$ and $R^2$ side groups. Preferably, all the coordinating hetero atoms are nitrogen atoms.

The ligand L of formula (B) preferably comprises at least two substituted or unsubstituted heteroaryl groups in the four side groups. The heteroaryl group is preferably a pyridin-2-yl group and, if substituted, preferably a methyl- or ethyl-substituted pyridin-2-yl group. More preferably, the heteroaryl group is an unsubstituted pyridin-2-yl group. Preferably, the heteroaryl group is linked to methylamine, and preferably to the N atom thereof, via a methylene group. Preferably, the ligand L of formula (B) contains at least one optionally substituted amino-alkyl side group, more preferably two amino-ethyl side groups, in particular 2-(N-alkyl)amino-ethyl or 2-(N,N-dialkyl)amino-ethyl.

Thus, in formula (B) preferably $R^1$ represents pyridin-2-yl or $R^2$ represents pyridin-2-yl-methyl. Preferably $R^2$ or $R^1$ represents 2-amino-ethyl, 2-(N-(m)ethyl)amino-ethyl or 2-(N,N-di(m)ethyl)amino-ethyl. If substituted, $R^5$ preferably represents 3-methyl pyridin-2-yl. $R^3$ preferably represents hydrogen, benzyl or methyl.

Examples of preferred ligands L of formula (B) in their simplest forms are:

(i) pyridin-2-yl containing ligands such as:

N,N-bis(pyridin-2-yl-methyl)-bis(pyridin-2-yl)methylamine;

N,N-bis(pyrazol-1-yl-methyl)-bis(pyridin-2-yl)methylamine;

N,N-bis(imidazol-2-yl-methyl)-bis(pyridin-2-yl)methylamine;

N,N-bis(1,2,4-triazol-1-yl-methyl)-bis(pyridin-2-yl)methylamine;

N,N-bis(pyridin-2-yl-methyl)-bis(pyrazol-1-yl)methylamine;

N,N-bis(pyridin-2-yl-methyl)-bis(imidazol-2-yl)methylamine;

N,N-bis(pyridin-2-yl-methyl)-bis(1,2,4-triazol-1-yl)methylamine;

N,N-bis(pyridin-2-yl-methyl)-1,1-bis(pyridin-2-yl)-1-aminoethane;

N,N-bis(pyridin-2-yl-methyl)-1,1-bis(pyridin-2-yl)-2-phenyl-1-aminoethane;

N,N-bis(pyrazol-1-yl-methyl)-1,1-bis(pyridin-2-yl)-1-aminoethane;

N,N-bis(pyrazol-1-yl-methyl)-1,1-bis(pyridin-2-yl)-2-phenyl-1-aminoethane;

N,N-bis(imidazol-2-yl-methyl)-1,1-bis(pyridin-2-yl)-1-aminoethane:

N,N-bis(imidazol-2-yl-methyl)-1,1-bis(pyridin-2-yl)-2-phenyl-1-aminoethane;

N,N-bis(1,2,4-triazol-1-yl-methyl)-1,1-bis(pyridin-2-yl)-1-aminoethane;

N,N-bis(1,2,4-triazol-1-yl-methyl)-1,1-bis(pyridin-2-yl)-2-phenyl-1-aminoethane;

N,N-bis(pyridin-2-yl-methyl)-1,1-bis(pyrazol-1-yl)-1-aminoethane;

N,N-bis(pyridin-2-yl-methyl)-1,1-bis(pyrazol-1-yl)-2-phenyl-1-aminoethane;

N,N-bis(pyridin-2-yl-methyl)-1,1-bis(imidazol-2-yl)-1-aminoethane;

N,N-bis(pyridin-2-yl-methyl)-1,1-bis(imidazol-2-yl)-2-phenyl-1-aminoethane;

N,N-bistpyridin-2-yl-methyl)-1,1-bis(1,2,4-triazol-1-yl)-1-aminoethane;

N,N-bis(pyridin-2-yl-methyl)-1,1-bis(1,2,4-triazol-1-yl)-1-aminoethane;

N,N-bis(pyridin-2-yl-methyl)-1,1-bis(pyridin-2-yl)-1-aminoethane;

N,N-bis(pyridin-2-yl-methyl)-1,1-bis(pyridin-2-yl)-1-aminohexane;

N,N-bis(pyridin-2-yl-methyl)-1,1-bis(pyridin-2-yl)-2-phenyl-1-aminoethane;

N,N-bis(pyridin-2-yl-methyl)-1,1-bis(pyridin-2-yl)-2-(4-sulphonic acid-phenyl)-1-aminoethane;

N,N-bis(pyridin-2-yl-methyl)-1,1-bis(pyridin-2-yl)-2-(pyridin-2-yl)-1-aminoethane;

N,N-bis(pyridin-2-yl-methyl)-1,1-bis(pyridin-2-yl)-2-(pyridin-3-yl)-1-aminoethane;

N,N-bis(pyridin-2-yl-methyl)-1,1-bis(pyridin-2-yl)-2-(pyridin-4-yl)-1-aminoethane;

N,N-bis(pyridin-2-yl-methyl)-1,1-bis(pyridin-2-yl)-2-(1-alkyl-pyridinium-4-yl)-1-aminoethane;

N,N-bis(pyridin-2-yl-methyl)-1,1-bis(pyridin-2-yl)-2-(1-alkyl-pyridinium-3-yl)-1-aminoethane;

N,N-bis(pyridin-2-yl-methyl)-1,1-bis(pyridin-2-yl)-2-(1-alkyl-pyridinium-2-yl)-1-aminoethane;

(ii) 2-amino-ethyl containing ligands such as:
N,N-bis(2-(N-alkyl)amino-ethyl)-bis(pyridin-2-yl)methylamine;
N,N-bis(2-(N-alkyl)amino-ethyl)-bis(pyrazol-1-yl)methylamine;
N,N-bis(2-(N-alkyl)amino-ethyl)-bis(imidazol-2-yl)methylamine;
N,N-bis(2-(N-alkyl)amino-ethyl)-bis(1,2,4-triazol-1-yl)methylamine;
N,N-bis(2-(N,N-dialkyl)amino-ethyl)-bis(pyridin-2-yl)methylamine;
N,N-bis(2-(N,N-dialkyl)amino-ethyl)-bis(pyrazol-1-yl)methylamine;
N,N-bis(2-(N,N-dialkyl)amino-ethyl)-bis(imidazol-2-yl)methylamine;
N,N-bis(2-(N,N-dialkyl)amino-ethyl)-bis(1,2,4-triazol-1-yl)methylamine;
N,N-bis(pyridin-2-yl-methyl)-bis(2-amino-ethyl)methylamine;
N,N-bis(pyrazol-1-yl-methyl)-bis(2-amino-ethyl)methylamine;
N,N-bis(imidazol-2-yl-methyl)-bis(2-amino-ethyl)methylamine;
N,N-bis(1,2,4-triazol-1-yl-methyl)-bis(2-amino-ethyl)methylamine.

More preferred ligands are:
N,N-bis(pyridin-2-yl-methyl)-bis(pyridin-2-yl)methylamine, hereafter referred to as N4Py.
N,N-bis(pyridin-2-yl-methyl)-1,1-bis(pyridin-2-yl)-1-aminoethane, hereafter referred to as MeN4Py,
N,N-bis(pyridin-2-yl-methyl)-1,1-bis(pyridin-2-yl)-2-phenyl-1-aminoethane, hereafter referred to as BzN4Py.

In an alternative fourth embodiment, the organic substance forms a complex of the general formula (A) including a ligand (B) as defined above, but with the proviso that $R^3$ does not represent hydrogen.

In a fifth embodiment of the second variant, the organic substance forms a complex of the general formula (A) as defined above, but wherein L represents a pentadentate or hexadentate ligand of general formula (C):

$$R^1R^1N-W-NR^1R^2$$

wherein
each $R^1$ independently represents $-R^3-V$, in which $R^3$ represents optionally substituted alkylene, alkenylene, oxyalkylene, aminoalkylene or alkylene ether, and V represents an optionally substituted heteroaryl group selected from pyridinyl, pyrazinyl, pyrazolyl, pyrrolyl, imidazolyl, benzimidazolyl, pyrimidinyl, triazolyl and thiazolyl;

W represents an optionally substituted alkylene bridging group selected from $-CH_2CH_2-$, $-CH_2CH_2CH_2-$, $-CH_2CH_2CH_2CH_2-$, $-CH_2-C_6H_4-CH_2-$, $-CH_2-C_6H_{10}-CH_2-$, and $-CH_2-C_{10}H_6-CH_2-$; and $R^2$ represents a group selected from $R^1$, and alkyl, aryl and arylalkyl groups optionally substituted with a substituent selected from hydroxy, alkoxy, phenoxy, carboxylate, carboxamide, carboxylic ester, sulphonate, amine, alkylamine and $N^+(R^4)_3$, wherein $R^4$ is selected from hydrogen, alkanyl, alkenyl, arylalkanyl, arylalkenyl, oxyalkanyl, oxyalkenyl, aminoalkanyl, aminoalkenyl, alkanyl ether and alkenyl ether.

The ligand L having the general formula (C), as defined above, is a pentadentate ligand or, if $R^1=R^2$, can be a hexadentate ligand. As mentioned above, by 'pentadentate' is meant that five hetero atoms can coordinate to the metal M ion in the metal-complex. Similarly, by 'hexadentate' is meant that six hetero atoms can in principle coordinate to the metal M ion. However, in this case it is believed that one of the arms will not be bound in the complex, so that the hexadentate ligand will be penta coordinating.

In the formula (C), two hetero atoms are linked by the bridging group W and one coordinating hetero atom is contained in each of the three $R^1$ groups. Preferably, the coordinating hetero atoms are nitrogen atoms.

The ligand L of formula (C) comprises at least one optionally substituted heteroaryl group in each of the three $R^1$ groups. Preferably, the heteroaryl group is a pyridin-2-yl group, in particular a methyl- or ethyl-substituted pyridin-2-yl group. The heteroaryl group is linked to an N atom in formula (C), preferably via an alkylene group, more preferably a methylene group. Most preferably, the heteroaryl group is a 3-methyl-pyridin-2-yl group linked to an N atom via methylene.

The group $R^2$ in formula (C) is a substituted or unsubstituted alkyl, aryl or arylalkyl group, or a group $R^1$. However, preferably $R^2$ is different from each of the groups $R^1$ in the formula above. Preferably, $R^2$ is methyl, ethyl, benzyl, 2-hydroxyethyl or 2-methoxyethyl. More preferably, $R^2$ is methyl or ethyl.

The bridging group W may be a substituted or unsubstituted alkylene group selected from $-CH_2CH_2-$, $-CH_2CH_2CH_2-$, $-CH_2CH_2CH_2CH_2-$, $-CH_2-C_6H_4-CH_2-$, $-CH_2-C_6H_{10}-CH_2-$, and $-CH_2-C_{10}H_6-CH_2-$ (wherein $-C_6H_4-$, $-C_6H_{10}-$, $-C_{10}H_6-$ can be ortho-, para-, or meta-$C_6H_4-$, $-C_6H_{10}-$, $-C_{10}H_6-$). Preferably, the bridging group W is an ethylene or 1,4-butylene group, more preferably an ethylene group.

Preferably, V represents substituted pyridin-2-yl, especially methyl-substituted or ethyl-substituted pyridin-2-yl, and most preferably V represents 3-methyl pyridin-2-yl.

Examples of preferred ligands of formula (C) in their simplest forms are:
N-methyl-N,N',N'-tris(3-methyl-pyridin-2-ylmethyl)ethylene-1,2-diamine;
N-ethyl-N,N',N'-tris(3-methyl-pyridin-2-ylmethyl)ethylene-1,2-diamine;
N-benzyl-N,N',N'-tris(3-methyl-pyridin-2-ylmethyl)ethylene-1,2-diamine;
N-(2-hydroxyethyl)-N,N',N'-tris(3-methyl-pyridin-2-ylmethyl)ethylene-1,2-diamine;
N-(2-methoxyethyl)-N,N',N'-tris(3 -methyl-pyridin-2-ylmethyl)ethylene-1,2-diamine;
N-methyl-N,N',N'-tris(5-methyl-pyridin-2-ylmethyl)ethylene-1,2-diamine;
N-ethyl-N,N',N'-tris(5-methyl-pyridin-2-ylmethyl)ethylene-1,2-diamine;
N-benzyl-N,N',N'-tris(5-methyl-pyridin-2-ylmethyl)ethylene-1,2-diamine;
N-(2-hydroxyethyl)-N,N',N'-tris(5-methyl-pyridin-2-ylmethyl)ethylene-1,2-diamine;
N-(2-methoxyethyl)-N,N',N'-tris(5-methyl-pyridin-2-ylmethyl)ethylene-1,2-diamine;

N-methyl-N,N',N'-tris(3-ethyl-pyridin-2-ylmethyl)
   ethylene-1,2-diamine;
N-ethyl-N,N',N'-tris(3-ethyl-pyridin-2-ylmethyl)
   ethylene-1,2-diamine;
N-benzyl-N,N',N'-tris(3-ethyl-pyridin-2-ylmethyl)
   ethylene-1,2-diamine;
N-(2-hydroxyethyl)-N,N',N'-tris(3-ethyl-pyridin-2-
   ylmethyl)ethylene-1,2-diamine;
N-(2-methoxyethyl)-N,N',N'-tris(3-ethyl-pyridin-2-
   ylmethyl)ethylene-1,2-diamine;
N-methyl-N,N',N'-tris(5-ethyl-pyridin-2-ylmethyl)
   ethylene-1,2-diamine;
N-ethyl-N,N',N'-tris(5-ethyl-pyridin-2-ylmethyl)
   ethylene-1,2-diamine;
N-benzyl-N,N',N'-tris(5-ethyl-pyridin-2-ylmethyl)
   ethylene-1,2-diamine; and
N-(2-methoxyethyl)-N,N',N'-tris(5-ethyl-pyridin-2-
   ylmethyl)ethylene-1,2-diamine.
More preferred ligands are:
N-methyl-N,N',N'-tris(3-methyl-pyridin-2-ylmethyl)
   ethylene-1,2-diamine;
N-ethyl-N,N',N'-tris(3-methyl-pyridin-2-ylmethyl)
   ethylene-1,2-diamine;
N-benzyl-N,N',N'-tris(3-methyl-pyridin-2-ylmethyl)
   ethylene-1,2-diamine;
N-(2-hydroxyethyl)-N,N',N'-tris(3-methyl-pyridin-2-
   ylmethyl)ethylene-1,2-diamine; and
N-(2-methoxyethyl)-N,N',N'-tris(3-methyl-pyridin-2-
   ylmethyl)ethylene-1,2-diamine.
The most preferred ligands are:
N-methyl-N,N',N'-tris(3-methyl-pyridin-2-ylmethyl)
   ethylene-1,2-diamine; and
N-ethyl-N,N',N'-tris(3-methyl-pyridin-2-ylmethyl)
   ethylene-1,2-diamine.

Preferably, the metal M in formula (A) is Fe or Mn, more preferably Fe.

Preferred coordinating species X in formula (A) may be selected from $R^6OH$, $NR^6_3$, $R^6CN$, $R^6OO^-$, $R^6S^-$, $R^6O^-$, $R^6COO^-$, $OCN^-$, $SCN^-$, $N_3^-$, $CN^-$, $F^-$, $Cl^-$, $Br^-$, $I^-$, $O^{2-}$, $NO_3^-$, $NO_2^-$, $SO_4^{2-}$, $SO_3^{2-}$, $PO_4^{3-}$ and aromatic N donors selected from pyridines, pyrazines, pyrazoles, pyrroles, imidazoles, benzimidazoles, pyrimidines, triazoles and thiazoles, with $R^6$ being selected from hydrogen, optionally substituted alkyl and optionally substituted aryl. X may also be the species $LMO^-$ or $LMOO^-$, wherein M is a transition metal and L is a ligand as defined above. The coordinating species X is preferably selected from $CH_3CN$, $H_2O$, $F^-$, $Cl^-$, $Br^-$, $OOH^-$, $R^6COO^-$, $R^6O^-$, $LMO^-$, and $LMOO^-$ wherein $R^6$ represents hydrogen or optionally substituted phenyl, naphthyl, or $C_1$—$C_4$ alkyl.

The counter ions Y in formula (A) balance the charge z on the complex formed by the ligand L, metal M and coordinating species X. Thus, if the charge z is positive, Y may be an anion such as $R^7COO^-$, $BPh_4^-$, $ClO_4^-$, $BF_4^-$, $PF_6^-$, $R^7SO_3^-$, $R^7SO_4^-$, $SO_4^{2-}$, $NO_3^-$, $F^-$, $Cl^-$, $Br^-$, or $I^-$, with $R^7$ being hydrogen, optionally substituted alkyl or optionally substituted aryl. If z is negative, Y may be a common cation such as an alkali metal, alkaline earth metal or (alkyl) ammonium cation.

Suitable counter ions Y include those which give rise to the formation of storage-stable solids. Preferred counter ions for the preferred metal complexes are selected from $R^7COO^-$, $ClO_4^-$, $BF_4^-$, $PF_6^-$, $R^7SO_3^-$ (in particular $CF_3SO_3^-$), $R^7SO_4^-$, $SO_4^{2-}$, $NO_3^-$, $F^-$, $Cl^-$, $Br^-$, and $I^-$, wherein $R^7$ represents hydrogen or optionally substituted phenyl, naphthyl or $C_1$–$C_4$ alkyl.

It will be appreciated that the complex (A) can be formed by any appropriate means, including in situ formation whereby precursors of the complex are transformed into the active complex of general formula (A) under conditions of storage or use. Preferably, the complex is formed as a well-defined complex or in a solvent mixture comprising a salt of the metal M and the ligand L or ligand L-generating species. Alternatively, the catalyst may be formed in situ from suitable precursors for the complex, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as $FeSO_4$ can be mixed in solution with the ligand L, or a ligand L-generating species, to form the active complex. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according the formula (A).

Therefore, in alternative fourth and fifth embodiments, the organic substance is a compound of the general formula (D):

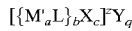

in which
   M' represents hydrogen or a metal selected from Ti, V, Co, Zn, Mg, Ca, Sr, Ba, Na, K, and Li;
   X represents a coordinating species;
   a represents an integer in the range from 1 to 5;
   b represents an integer in the range from 1 to 4;
   c represents zero or an integer in the range from 0 to 5;
   z represents the charge of the compound and is an integer which can be positive, zero or negative;
   Y represents a counter ion, the type of which is dependent on the charge of the compound;
   q=z/[charge Y]; and
   L represents a pentadentate ligand of general formula (B) or (C) as defined above.

In a fourth embodiment of the first variant, the organic substance comprises a macrocyclic ligand of formula (E):

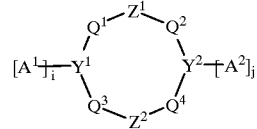

wherein
   $Z^1$ and $Z^2$ are independently selected from monocyclic or polycyclic aromatic ring structures optionally containing one or more heteroatoms, each aromatic ring structure being substituted by one or more substituents;
   $Y^1$ and $Y^2$ are independently selected from C, N, O, Si, P and S atoms;
   $A^1$ and $A^2$ are independently selected from hydrogen, alkyl, alkenyl and cycloalkyl (each of alkyl, alkenyl and cycloalkyl) being optionally substituted by one or more groups selected from hydroxy, aryl, heteroaryl, sulphonate, phosphate, electron donating groups and electron withdrawing groups, and groups of formulae $(G^1)(G^2)N$—, $G^3OC(O)$—, $G^3O$— and $G^3C(O)$—, wherein each of $G^1$, $G^2$ and $G^3$ is independently selected from hydrogen and alkyl, and electron donating and/or withdrawing groups (in addition to any amongst the foregoing);

i and j are selected from 0, 1 and 2 to complete the valency of the groups $Y^1$ and $y^2$;

each of $Q^1$–$Q^4$ is independently selected from groups of formula

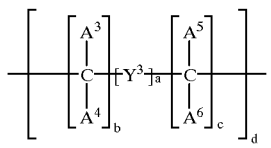

wherein 10>a+b+c>2 and d>=1;

each $Y^3$ is independently selected from —O—, —S—, —SO—, —SO$_2$—, —(G')N— (wherein $G^1$ is hereinbefore defined), —C(O)—, arylene, heteroarylene, —P— and —P(O)—;

each of $A^3$–$A^6$ is independently selected from the groups hereinbefore defined for $A^1$ and $A^2$; and wherein any two or more of $A^1$–$A^6$ together form a bridging group, provided that if $A^1$ and $A^2$ are linked without simultaneous linking also to any of $A^3$–$A^6$, then the bridging group linking $A^1$ and $A^2$ must contain at least one carbonyl group.

In the ligands of formula (E), unless specifically stated to the contrary, all alkyl, hydroxyalkyl alkoxy, and alkenyl groups preferably have from 1 to 6, more preferably from 1 to 4 carbon atoms.

Moreover, preferred electron donating groups include alkyl (e.g. methyl), alkoxy (e.g. methoxy), phenoxy, and unsubstituted, monosubstituted and disubstituted amine groups. Preferred electron withdrawing groups include nitro, carboxy, sulphonyl and halo groups.

The ligands of formula (E) may be used in the form of complexes with an appropriate metal or, in some cases, in non-complexed form. In the non-complexed form, they rely upon complexing with a metal supplied in the form of a separate ingredient in the composition, specifically provided for supplying that metal, or upon complexing with a metal found as a trace element in tap water. However, where the ligand alone or in complex form carries a (positive) charge, a counter anion is necessary. The ligand or complex may be formed as a neutral species but it is often advantageous, for reasons of stability or ease of synthesis, to have a charged species with appropriate anion.

Therefore, in an alternative fourth embodiment, the ligand of formula (E) is ion-paired with a counter ion, which ion-pairing is denoted by formula (F):

[H$_x$L]$Y_q$ wherein

H is an hydrogen atom;

Y is a counter anion, the type of which is dependent on the charge of the complex;

x is an integer such that one or more nitrogen atoms in L is protonated;

z represents the charge of the complex and is an integer which can be positive or zero;

q=z/[charge of Y]; and

L is a ligand of formula (E) as defined above.

In a further alternative fourth embodiment, the organic substance forms a metal complex of formula (G) based on the ion pairing of formula (F) thus:

[M$_x$L]$Y_q$ wherein L, Y, x, z and q are as defined for formula (F) above and M is a metal selected from manganese in oxidation states II–V, iron II–V, copper I–III, cobalt I–III, nickel I–III, chromium II–VI, tungsten IV–VI, palladium V, ruthenium II–IV, vanadium III–IV and molybdenum IV–VI.

Especially preferred are the complexes of formula (G) wherein M represents manganese, cobalt, iron or copper.

In a preferred fourth embodiment, the organic substance forms a complex of the formula (H):

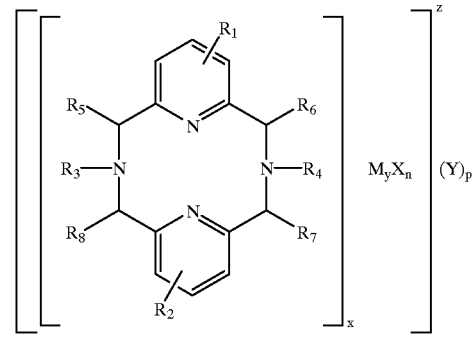

wherein M represents an iron atom in oxidation state II or III, a manganese atom in oxidation state II, III, IV or V, a copper atom in oxidation state I, II or III or a cobalt atom in oxidation state II, III or IV, X is a group which is either a bridge or is not a bridge between iron atoms, Y is a counter ion, x and y being >=1, 0=<n=<3, and z being the charge of the metal complex, and p=z/ charge of Y; $R_1$ and $R_2$ being independently one or more ring substituents selected from hydrogen and electron donating and withdrawing groups, $R_3$ to $R_8$ being independently hydrogen, alkyl, hydroxyalkyl, alkenyl or variants of any of these when substituted by one or more electron donating or withdrawing groups.

For the avoidance of doubt, "=<" means "less than or equal to" and ">=" means "greater than or equal to".

Preferably, in the complex of formula (H), M represents an iron atom in oxidation state II or III or a manganese atom in oxidation state II, III, IV, or V. Preferably the oxidation state of M is III.

When M is iron, preferably the complex of formula (H) is in the form of a salt of iron (in oxidised state) dihalo-2,11 -diazo[3.3](2,6)pyridinophane, dihalo-4-methoxy-2,11-diazo[3.3] (2,6) pyridinophane and mixtures thereof, especially in the form of the chloride salt.

When M is manganese, preferably the complex of formula (H) is in the form of a salt of manganese (in oxidised state) N, N'-dimethyl-2,11-diazo[3.3](2,6)pyridinophane, especially in the form of the monohexafluorophosphate salt.

Preferably, X is selected from H$_2$O, OH$^-$, O$^{2-}$, SH$^-$, S$^{2-}$, SO$_4^{2-}$, NR$_9$R$_{10}^-$, RCOO$^-$, NR$_9$R$_{10}$R$_{11}$, Cl$^-$, Br$^-$, F$^-$, N$_3^-$ and combinations thereof, wherein R$_9$, R$_{10}$ and R$_{11}$ are independently selected from —H, C$_{1-4}$ alkyl and aryl optionally substituted by one or more electron withdrawing and/or donating groups. More preferably, X is a halogen, especially a fluoride ion.

In the formulae (F), (G) and (H), the anionic counter ion equivalent Y is preferably selected from Cl$^-$, Br$^-$, I$^-$, NO$_3^-$, $ClO_4^-$, $SCN^-$, $PF_6^-$, $RSO_3^-$, $RSO_4^-$, $CF_3SO_3^-$, $BPh_4^-$, and $OAc^-$. A cationic counter ion equivalent is preferably absent.

In formula (H), $R_1$ and $R_2$ are preferably both hydrogen. $R_3$ and $R_4$ are preferably $C_{1-4}$ alkyl, especially methyl. $R_5$–$R_8$ are each preferably hydrogen.

According to the values of x and y, the aforementioned preferred iron or manganese catalysts of formula (H) may be in the form of a monomer, dimer or oligomer. Without being bound by any theory, it has been conjectured that in the raw material or detergent composition state, the catalyst exists mainly or solely in monomer form but could be converted to dimer, or even oligomeric form, in the wash solution.

The bleaching compositions according to the present invention may be used for laundry cleaning, hard surfaces cleaning (including cleaning of lavatories, kitchen work surfaces, floors, mechanical ware washing etc.). As is generally known in the art, bleaching compositions are also employed waste-water treatment, pulp bleaching during the manufacture of paper, leather manufacture, dye transfer inhibition, food processing, starch bleaching, sterilisation, whitening in oral hygiene preparations and/or contact lens disinfection. In the context of the present invention bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate.

In typical washing compositions the level of the organic substance is such that the in-use level is from 1 $\mu$M to 50 mM, with preferred in-use levels for domestic laundry operations falling in the range 10 to 100 $\mu$M. Higher levels may be desired and applied in industrial bleaching processes, such as textile and paper pulp bleaching.

Preferably, the aqueous medium has a pH in the range from pH 6 to 13, more preferably from pH 6 to 11, still more preferably from pH 8 to 11, and most preferably from pH 8 to 10, in particular from pH 9 to 10.

The bleaching composition of the present invention has particular application in detergent formulations, especially for laundry cleaning. Accordingly, in another preferred embodiment, the present invention provides a detergent bleach composition comprising a bleaching composition as defined above and additionally a surface-active material, optionally together with detergency builder.

The bleach composition according to the present invention may for example contain a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulphates and sulphonates having alkyl groups containing from about 8 to about 22 carbon atoms, the term "alkyl" being used to include the alkyl portion of higher aryl groups. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those ethers of the higher alcohols derived from tallow or coconut oil fatty acid monoglyceride sulphates and sulphonates; sodium and ammonium salts of sulphuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolysing with a base to produce a random sulphonate; sodium and ammonium ($C_7$–$C_{12}$) dialkyl sulphosuccinates; and olefin sulphonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulphonates, and sodium ($C_{16}$–$C_{18}$) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

The detergent bleach composition of the invention will preferably comprise from 1 to 15% wt of anionic surfactant and from 10 to 40% by weight of nonionic surfactant. In a further preferred embodiment, the detergent active system is free from $C_{16}$–$C_{12}$ fatty acid soaps.

The bleach composition of the present invention may also contains a detergency builder, for example in an amount of from about 5 to 80% by weight, preferably from about 10 to 60% by weight.

Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid, and polyacetal carboxylates as disclosed in U.S. Pat. No. 4,144, 226 and U.S. Pat. No. 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions of the invention may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

It is preferred that the composition contains not more than 5% by weight of a carbonate builder, expressed as sodium carbonate, more preferably not more than 2.5% by weight to substantially nil, if the composition pH lies in the lower alkaline region of up to 10.

Apart from the components already mentioned, the bleach composition of the present invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulphate and sodium silicate; and, usually in very small amounts, fluorescent agents; perfumes; enzymes, such as proteases, cellulases, lipases, amylases and oxidases; germicides and colourants.

Transition metal sequestrants such as EDTA, and phosphonic acid derivatives such as EDTMP (ethylene diamine tetra(methylene phosphonate)) may also be included, in addition to the organic substance specified, for example to improve the stability sensitive ingredients such as enzymes, fluorescent agents and perfumes, but provided the composition remains bleaching effective. However, the composition according to the present invention containing the organic substance, is preferably substantially, and more preferably completely, devoid of transition metal sequestrants (other than the organic substance).

Whilst the present invention is based on the catalytic bleaching of a substrate by atmospheric oxygen or air, it will be appreciated that small amounts of hydrogen peroxide or peroxy-based or -generating systems may be included in the composition, if desired. Therefore, by "substantially devoid of peroxygen bleach or peroxy-based or -generating bleach systems" is meant that the composition contains from 0 to 50%, preferably from 0 to 10%, more preferably from 0 to 5%, and optimally from 0 to 2% by molar weight on an oxygen basis, of peroxygen bleach or peroxy-based or -generating bleach systems. Preferably, however, the composition will be wholly devoid of peroxygen bleach or peroxy-based or -generating bleach systems.

Thus, at least 10%, preferably at least 50% and optimally at least 90% of any bleaching of the substrate is effected by oxygen sourced from the air.

The invention will now be further illustrated by way of the following non-limiting examples:

EXAMPLES

Example 1

This example describes a synthesis of a catalyst according to formula (A):

(i) Preparation of MeN4Py Ligand:

The precursor N4Py.HClO$_4$ was prepared as follows:

To pyridyl ketone oxim (3 g, 15.1 mmol) was added ethanol (15 ml), concentrated ammonia solution (15 mL) and NH$_4$OAc (1.21 g, 15.8 mmol). The solution was warmed until reflux. To this solution was added 4.64 g Zn in small portions. After the addition of all Zn, the mixture was refluxed for 1 hour and allowed to cool to ambient temperature. The solution was filtered and water (15 ml) was added. Solid NaOH was added until pH>>10 and the solution was extracted with CH$_2$Cl$_2$ (3×20 ml). The organic layers were dried over Na$_2$SO$_4$ and evaporated until dryness. Bis(pyridin-2-yl)methylamine (2.39 g, 12.9 mmol) was obtained as a colourless oil in 86% yield, showing the following analytical characteristics:

$^1$H NMR (360 MHz, CDCl$_3$): δ 2.64 (s, 2H, NH$_2$), 5.18 (s, 1H, CH), 6.93 (m, 2H, pyridine), 7.22 (m, 2H, pyridine), 7.41 (m, 2H, pyridine), 8.32 (m, 2H, pyridine); $^{13}$C NMR (CDCl$_3$): δ 62.19 (CH), 121.73 (CH), 122.01 (CH), 136.56 (CH), 149.03 (CH), 162.64 (Cq).

To picolylchloride hydrochloride (4.06 g, 24.8 mmol) was added, at 0° C., 4.9 ml of a 5N NaOH solution. This emulsion was added by means of a syringe to bis(pyridin-2-yl)methylamine (2.3 g, 12.4 mmol) at 0° C. Another 5 ml of a 5N NaOH solution was added to this mixture. After warming to ambient temperature, the mixture was stirred vigorously for 40 hrs. The mixture was put in an ice bath and HClO$_4$ was added until pH<1, whereupon a brown solid precipitated. The brown precipitate was collected by filtration and recrystallized from water. While stirring, this mixture was allowed to cool to ambient temperature. whereupon a light-brown solid precipitated which was collected by filtration and washed with cold water and air-dried (1.47 g).

From 0.5 g of the perchlorate salt of N4Py prepared as described above, the free amine was obtained by precipitating the salt with 2N NaOH and subsequently by extraction with CH$_2$Cl$_2$. To the free amine was added under argon 20 ml of dry tetrahydrofuran freshly distilled from LiAlH$_4$. The mixture was stirred and cooled to −70° C. by an alcohol/dry ice bath. Now 1 ml of 2.5 N butyllithium solution in hexane was added giving an immediate dark red colour. The mixture was allowed to warm to −20° C. and now 0.1 ml of methyl iodide was added. The temperature was kept to −10° C. for 1 hour. Subsequently 0.5 g of ammonium chloride was added and the mixture was evaporated in vacuo. To the residue water was added and the aqueous layer was extracted with dichloromethane. The dichloromethane layer was dried on sodium sulphate, filtered and evaporated giving 0.4 g residue. The residue was purified by crystallisation from ethyl acetate and hexane giving 0.2 g of creamish powder (50% yield) showing the following analytical characteristics:

$^1$H NMR (400 MHz, CDCl$_3$): δ (ppm) 2.05 (s, 3H, CH$_3$), 4.01 (s, 4H, CH$_2$), 6.92 (m, 2H, pyridine), 7.08 (m, 2H, pyridine), 7.39 (m, 4H pyridine), 7.60 (m 2H, pyridine), 7.98 (d, 2H, pyridine), 8.41 (m, 2H pyridine), 8.57 (m, 2H, pyridine). $^{13}$C NMR (100.55 MHz, CDCl$_3$): δ (ppm) 21.7 (CH$_3$), 58.2 (CH$_2$), 73.2 (Cq), 121.4 (CH), 121.7 (CH), 123.4 (CH), 123.6 (CH), 136.0 (CH), 148.2 (Cq), 148.6 (Cq), 160.1 (Cq), 163.8 (Cq).

(ii) Synthesis of the Complex [(MeN4Py)Fe(CH$_3$CN)](ClO$_4$)$_2$, Fe(MeN4Py):

To a solution of 0.27 g of MeN4Py in 12 ml of a mixture of 6 ml acetonitrile and 6 ml methanol was added 350 mg Fe(ClO$_4$)$_2$.6H$_2$O immediately a dark red colour formed. To the mix was added now 0.5 g of sodium perchlorate and a orange red precipitate formed immediately. After 5 minutes stirring and ultrasonic treatment the precipitate was isolated by filtration and dried in vacuo at 50° C. In this way 350 mg of an orange red powder was obtained in 70% yield showing the following analytical characteristics:

$^1$H NMR (400 MHz, CD$_3$CN): δ (ppm) 2.15, (CH$_3$CN), 2.28 (s, 3H, CH$_3$), 4.2 (ab, 4H, CH$_2$), 7.05 (d, 2H, pyridine), 7.38 (m, 4H, pyridine), 7.71 (2t, 4H pyridine), 7.98 (t, 2H, pyridine), 8.96 (d, 2H pyridine), 9.06 (m, 2H, pyridine). UV/Vis (acetonitrile) [λmax, nm (ε, M$^{-1}$ cm$^{-1}$)]: 381 (8400), 458 nm (6400). Anal.Calcd for C$_{25}$H$_{26}$Cl$_2$FeN$_6$O$_8$: C, 46.11; H, 3.87; N, 12.41; Cl, 10.47; Fe, 8.25. Found: C, 45.49; H, 3.95; N, 12.5; Cl, 10.7; Fe, 8.12. Mass-ESP (cone voltage 17V in CH$_3$CN): m/z 218.6 [MeN4PyFe]$^{2+}$; 239.1 [MeN4PyFeCH$_3$CN]$^{2+}$.

Example 2

This example describes a synthesis of a catalyst according to formula (A):
(i) Synthesis of BzN4Py Ligand:

To 1 g of the N4Py ligand prepared as described above, 20 ml of dry tetrahydrofuran freshly distilled from LiAlH$_4$, was added under argon. The mixture was stirred and cooled to −70° C. by an alcohol/dry ice bath. Now 2 ml of 2.5 N butyllithium solution in hexane was added giving an immediate dark red colour. The mix was allowed to warm to −20° C. and now 0.4 ml of benzyl bromidide was added. The mixture was allowed to warm up to 25° C. and stirring was continued over night. Subsequently 0.5 g of ammonium chloride was added and the mixture was evaporated in vacuo. To the residue water was added and the aqueous layer was extracted with dichloromethane. The dichloromethane layer was dried on sodium sulphate, filtered and evaporated giving 1 g brown oily residue. According to NMR spectroscopy, the product was not pure but contained no starting material (N4Py). The residue was used without further purification.
(ii) Synthesis of the Complex [(BzN4Py)Fe(CH$_3$CN)] (ClO$_4$)$_2$, Fe(BzN4Py):

To a solution of 0.2 g of the residue obtained by the previous described procedure in 10 ml of a mixture of 5 ml acetonitrile and 5 ml methanol was added 100 mg Fe(ClO$_4$)$_2$.6H$_2$O immediately a dark red colour formed. To the mix was added now 0.25 g of sodium perchlorate and ethylacetate was allowed to diffuse into the mixture overnight. Some red crystals were formed which were isolated by filtration and washed with methanol. In this way 70 mg of a red powder was obtained showing the following analytical characteristics:

1H NMR (400 MHz, CD$_3$CN): δ (ppm) 2.12, (s, 3H, CH$_3$CN), 3.65+4.1 (ab, 4H, CH$_2$), 4.42 (s, 2H, CH$_2$-benzyl), 6.84 (d, 2H, pyridine), 7.35 (m, 4H, pyridine), 7.45 (m, 3 H, benzene) 7.65 (m, 4H benzene+pryidine), 8.08(m, 4H, pyridine), 8.95 (m, 4H pyridine). UV/Vis (acetonitrile) [λmax, nm (ε, M$^{-1}$ cm$^{-1}$)]: 380 (7400), 458 nm (5500). Mass-ESP (cone voltage 17V in CH3CN): m/z 256.4 [BzN4Py]$^{2+}$; 612 [BzN4PyFeClO$_4$]$^+$.

Example 3

This example describes syntheses of catalysts according to formula (C):

All reactions were performed under a nitrogen atmosphere, unless indicated otherwise. All reagents and solvents were obtained from Aldrich or Across and used as received, unless stated otherwise. Petroleum ether 40–60 was distilled using a rotavapor before using it as eluent. Flash column chromatography was performed using Merck silica gel 60 or aluminium oxide 90 (activity II–III according to Brockmann). $^1$H NMR (300 MHz) and $^{13}$C NMR (75 MHz) were recorded in CDCl$_3$, unless stated otherwise. Multiplicities were addressed with the normal abbreviations using p for quintet.
Synthesis of Starting Materials for Ligand Synthesis:

Synthesis of N-benzyl amino acetonitrile. N-benzyl amine (5.35 g, 50 mmol) was dissolved in a water: methanol mixture (50 mL, 1:4). Hydrochloric acid (aq., 30%) was added until the pH reached 7.0. Added was NaCN (2.45 g, 50 mmol). After cooling to 0° C., formaline (aq. 35%, 4.00 g, 50 mmol) was added. The reaction was followed by TLC (aluminium oxide; EtOAc:Et$_3$N=9:1) until benzylamine could be detected. Subsequently the methanol was evaporated in vacuo and the remaining oil "dissolved" in water. The aqueous phase was extracted with methylene chloride (3×50 mL). The organic layers were collected and the solvent removed in vacuo. The residue was purified by Kugelrohr distillation (p=20 mm Hg, T=120° C.) giving N-benzyl amino acetonitrile (4.39 g, 30 mmol, 60%) as a colourless oil.

$^1$H NMR: δ 7.37–7.30 (m, 5H), 3.94 (s, 2H), 3.57 (s, 2H), 1.67 (br s, 1H); $^{13}$C NMR: δ 137.74, 128.58, 128.46, 128.37, 127.98, 127.62, 117.60, 52.24, 36.19.

Synthesis of N-ethyl amino acetonitrile. This synthesis was performed analogously to the synthesis reported for N-benzyl amino acetonitrile. However, detection was done by dipping the TLC plate in a solution of KMnO$_4$ and heating the plate until bright spots appeared. Starting from ethylamine (2.25 g, 50 mmol), pure N-ethyl amino acetonitrile (0.68 g, 8.1 mmol, 16%) was obtained as a slightly yellow oil.

$^1$H NMR: δ 3.60 (s, 2H), 2.78 (q, J=7.1, 2H), 1.22 (br s, 1H), 1.14 (t, J=7.2, 3H); $^{13}$C NMR: δ 117.78, 43.08, 37.01, 14.53.

Synthesis of N-ethyl ethylene-1,2-diamine. The synthesis was performed according to Hageman; J.Org.Chem.; 14; 1949; 616, 634, starting from N-ethyl amino acetonitrile.

Synthesis of N-benzyl ethylene-1,2-diamine. Sodium hydroxide (890 mg; 22.4 mmol) was dissolved in ethanol (96%, 20 mL), the process taking the better part of 2 hours. Added was N-benzyl amino acetonitrile (4, 2.92 g, 20 mmol) and Raney Nickel (approx. 0.5 g). Hydrogen pressure was applied (p=3.0 atm.) until hydrogen uptake ceased. The mixture was filtered over Cellite, washing the residue with ethanol. The filter should not run dry since Raney Nickel is relatively pyrophoric. The Cellite containing the Raney Nickel was destroyed by putting the mixture in dilute acid, causing gas formation). The ethanol was evaporated in in vacuo and the residue dissolved in water. Upon addition of base (aq. NaOH, 5N) the product oiled out and was extracted with chloroform (3×20 mL). After evaporation of the solvent in vacuo the $^1$H NMR showed the presence of benzylamine. Separation was enforced by column chromatography (silica gel; MeOH:EtOAc:Et$_3$N=1:8:1) yielding the benzyl amine, followed by the solvent mixture MeOH:EtOAc:Et$_3$N=5:4:1. Detection was done by using aluminium oxide as a solid phase in TLC, yielding pure N-benzyl ethylene-1,2-diamine (2.04 g, 13.6 mmol, 69%).

$^1$H NMR: δ 7.33–7.24 (m, 5H), 3.80 (s, 2H), 2.82 (t, J=5.7, 2H), 2.69 (t, J=5.7, 2H), 1.46 (br s, 3H); $^{13}$C NMR: δ 140.37, 128.22, 127.93, 126.73, 53.73, 51.88, 41.66.

Synthesis of 2-acetoxymethyl-5-methyl pyridine. 2,5-Lutidine (31.0 g, 290 mmol), acetic acid (180 mL) and hydrogen peroxide (30 mL, 30%) were heated at 70–80° C. for 3hours. Hydrogen peroxide (24 mL, 30%) was added and the subsequent mixture heated for 16 hours at 60–70° C. Most of the mixture of (probably) hydrogen peroxide, water, acetic acid, and peracetic acid was removed in vacuo (rotavap, water bath 50° C. until p=20 mbar). The resulting mixture containing the N-oxide was added dropwise to acetic anhydride heated under reflux. This reaction was highly exothermic, and was controlled by the dropping speed. After heating under reflux for an hour, methanol was added dropwise. This reaction was highly exothermic. The resulting mixture was heated under reflux for another 30 minutes. After evaporation of the methanol (rotavap, 50° C. until p=20 mbar), the resulting mixture was purified by Kugelrohr distillation (p=20 mm Hg, T=150° C.). The clear oil that was obtained still contained acetic acid. This was removed by extraction ($CH_2Cl_2$, $NaHCO_3$ (sat.)) yielding the pure acetate of 2-acetoxymethyl-5-methyl pyridine (34.35 g, 208 mmol, 72%) as a slightly yellow oil.

$^1$H NMR: δ 8.43 (s, 1H), 7.52 (dd, J=7.8, J=1.7, 1H), 7.26 (d, J=7.2 1H), 5.18 (s, 2H), 2.34 (s, 3H), 2.15 (s, 3H); $^{13}$C NMR: δ 170.09, 152.32, 149.39, 136.74, 131.98, 121.14, 66.31, 20.39, 17.66.

Synthesis of 2-acetoxymethyl-5-ethyl pyridine. This synthesis was performed analogously to the synthesis reported for 2-acetoxymethyl-5-methyl pyridine. Starting from 5-ethyl-2-methyl pyridine (35.10 g, 290 mmol), pure 2-acetoxymethyl-5-ethyl pyridine (46.19 g, 258 mmol, 89%) was obtained as a slightly yellow oil.

$^1$H NMR: δ 8.47 (s, 1H), 7.55 (d, J=7.8, 1H), 7.29 (d, J=8.1, 1H), 2.67 (q, J=7.8, 2H), 2.14 (s, 3H), 1.26 (t, J=7.77, 3H); $^{13}$C NMR: δ 170.56, 152.80, 149.11, 138.47, 135.89, 121.67, 66.72, 25.65, 20.78, 15.13.

Synthesis of 2-acetoxymethyl-3-methyl pyridine. This synthesis was performed analogously to the synthesis reported for 2-acetoxymethyl-5-methyl pyridine. The only difference was the reversal of the Kugelrohr distillation and the extraction. According to $^1$H NMR a mixture of the acetate and the corresponding alcohol was obtained. Starting from 2,3-picoline (31.0 g, 290 mmol), pure 2-acetoxymethyl-3-methyl pyridine (46.19 g, 258 mmol, 89%, calculated for pure acetate) was obtained as a slightly yellow oil.

$^1$H NMR: δ 8.45 (d, J=3.9, 1H), 7.50 (d, J=8.4, 1H), 7.17 (dd, J=7.8, J=4.8, 1H), 5.24 (s, 2H), 2.37 (s, 3H), 2.14 (s, 3H).

Synthesis of 2-hydroxymethyl-5-methyl pyridine. 2-Acetoxymethyl-5-methyl pyridine (30 g, 182 mmol) was dissolved in hydrochloric acid (100 mL, 4 N). The mixture was heated under reflux, until TLC (silica gel; triethylamine:ethyl acetate:petroleum ether 40–60=1:9:19) showed complete absence of the acetate (normally 1 hour). The mixture was cooled, brought to pH>11, extracted with dichloromethane (3×50 mL) and the solvent removed in vacuo. Pure 2-hydroxymethyl-5-methyl pyridine (18.80 g, 152 mmol, 84%) was obtained by Kugelrohr distillation (p=20 mm Hg, T=130° C.) as a slightly yellow oil.

$^1$HNMR: δ 8.39(s, 1H),7.50(dd, J=7.8, J=1.8, 1H),7.15 (d, J=8.1, 1H),4.73 (s, 2H), 3.83 (br s, 1H), 2.34 (s, 3H); $^{13}$C NMR: δ 156.67, 148.66, 137.32, 131.62, 120.24, 64.12, 17.98.

Synthesis of 2-hydroxymethyl-5-ethyl pyridine. This synthesis was performed analogously to the synthesis reported for 2-hydroxymethyl-5-methyl pyridine. Starting from 2-acetoxymethyl-5-ethyl pyridine (40 g, 223 mmol), pure 2-hydroxymethyl-5-ethyl pyridine (26.02 g, 189 mmol, 85%) was obtained as a slightly yellow oil.

$^1$H NMR: δ 8.40 (d, J=1.2, 1H), 7.52 (dd, J=8.0, J=2.0, 1H), 7.18 (d, J=8.1, 1H), 4.74 (s, 2H), 3.93 (br s, 1H), 2.66 (q, J=7.6, 2H), 1.26 (t, J=7.5, 3H); $^{13}$C NMR: δ 156.67, 148.00, 137.87, 136.13. 120.27, 64.07, 25.67, 15.28.

Synthesis of 2-hydroxymethyl-3-methyl pyridine. This synthesis was performed analogously to the synthesis reported for 2-hydroxymethyl-5-methyl pyridine. Starting from 2-acetoxymethyl-3-methyl pyridine (25g (recalculated for the mixture), 152 mmol), pure 2-hydroxymethyl-3-methyl pyridine (15.51 g, 126 mmol, 83%) was obtained as a slightly yellow oil.

$^1$H NMR: δ 8.40 (d, J=4.5, 1H)), 7.47 (d, J=7.2, 1H), 7.15 (dd, J=7.5, J=5.1, 1H), 4.85 (br s, 1H), 4.69 (s, 1H), 2.22 (s, 3H); $^{13}$C NMR: δ 156.06, 144.97, 137.38, 129.53, 121.91, 61.38, 16.30.

(i) Synthesis of Ligands:

Synthesis of N-methyl-N,N',N'-tris(pyridin-2-ylmethyl) ethylene-1,2-diamine (L1). The ligand L1 (comparative) was prepared according to Bemal, Ivan; Jensen, Inge Margrethe; Jensen, Kenneth B.; McKenzie, Christine J.; Toftlund, Hans: Tuchagues, Jean-Pierre; J.Chem.Soc.Dalton Trans.; 22; 1995; 3667–3676.

Synthesis of N-methyl-N,N',N'-tris(3-methylpyridin-2-ylmethyl)ethylene-1,2-diamine (L2, MeTrilen). 2-Hydroxymethyl-3-methyl pyridine (5.00 g, 40.7 mmol) was dissolved in dichloromethane (30 mL). Thionyl chloride (30 mL) was added dropwise under cooling (ice bath). The resulting mixture was stirred for 1 hour and the solvents removed in vacuo (rotavap, until p=20 mm Hg, T=50° C.). To the resultant mixture was added dichloromethane (25 mL). Subsequently NaOH (5 N, aq.) was added dropwise until the pH (aqua)≧11. The reaction was quite vigorous in the beginning, since part of the thionyl chloride was still present. N-methyl ethylene-1,2-diamine (502 mg, 6.8 mmol) and additional NaOH (5 N, 10 mL) were added. The reaction mixture was stirred at room temperature for 45 hours. The mixture was poured into water (200 mL), and the pH checked (≧14, otherwise addition of NaOH (aq. 5N)). The reaction mixture was extracted with dichloromethane (3 or 4×50 mL, until no product could be detected by TLC). The combined organic phases were dried and the solvent removed in vacuo. Purification was enforced as described before, yielding N-methyl-N,N',N'-tris(3-methylpyridin-2-ylmethyl)ethylene-1,2-diamine as a slightly yellow oil. Purification was enforced by column chromatography (aluminium oxide 90 (activity II–III according to Brockmann); triethylamine:ethyl acetate:petroleum ether 40–60=1:9:10) until the impurities were removed according to TLC (aluminium oxide, same eluent, Rf≈0.9). The compound was eluted using ethylacetate:triethyl amine=9:1. N-methyl-N,N',N'-tris(3 -methylpyridin-2-ylmethyl) ethylene-1,2-diamine (L2, 1.743 g, 4.30 mmol, 63%) was obtained.

$^1$H NMR: δ 8.36 (d, J=3.0, 3H), 7.40–7.37 (m, 3H), 7.11–7.06 (m, 3H), 3.76 (s, 4H), 3.48 (s, 2H), 2.76–2.71 (m, 2H), 2.53–2.48 (m, 2H), 2.30 (s, 3H), 2.12 (s, 6H), 2.05 (s, 3H); $^{13}$C NMR: δ 156.82, 156.77, 145.83, 145.67, 137.61, 133.14, 132.72, 122.10, 121.88, 62.32, 59.73, 55.19, 51.87, 42.37, 18.22, 17.80.

Synthesis of N-ethyl-N,N',N'-tris(3-methylpyridin-2-ylmethyl)ethylene-1,2-diamine (L3, EtTrilen). This synthesis is performed analogously to the synthesis for L2. Starting from 2-hydroxymethyl-3-methyl pyridine (25.00 g, 203 mmol) and N-ethyl ethylene-1,2-diamine (2.99 g, 34.0 mmol), N-ethyl-N,N',N'-tris(methylpyridin-2-ylmethyl) ethylene-1,2-diamine (L3, 11.49 g, 28.5 mmol, 84%) was obtained. Column chromatography (aluminium oxide; Et$_3$N:

EtOAc: petroleum ether 40–60=1:9:30, followed by Et₃N:EtOAc=1:9).

¹H NMR: δ 8.34–8.30 (m, 3H), 7.40–7.34 (m, 3H), 7.09–7.03 (m, 3H), 3.71 (s, 4H), 3.58 (s, 2H), 2.64–2.59 (m, 2H), 2.52–2.47 (m, 2H), 2.43–2.36 (m, 2H), 2.31 (s, 3H), 2.10 (s, 6H), 0.87 (t, J=7.2, 3H); ¹³C NMR: δ 157.35, 156.92, 145.65, 137.61, 133.14, 132.97, 122.09, 121.85, 59.81, 59.28, 51.98, 50.75, 48.02, 18.27, 17.80, 11.36.

Synthesis of N-benzyl-N,N',N'-tris(3-methylpyridin-2-ylmethyl)ethylene-1,2-diamine (L4, BzTrilen). This synthesis is performed analogously to the synthesis for L2. Starting from 2-hydroxymethyl-3-methylpyridine (3.00 g 24.4 mmol), and N-benzyl ethylene-1,2-diamine (610 mg, 4.07 mmol), N-benzyl-N,N',N'-tris(3-methylpyridin-2-ylmethyl)ethylene-1,2-diamine (L4, 1.363 g, 2.93 mmol, 72%) was obtained. Column chromatography (aluminium oxide; Et₃N:EtOAc:petroleum ether 40–60=1:9:10).

¹H NMR: δ 8.33–8.29 (m, 3H), 7.37–7.33 (m, 3H), 7.21–7.03 (m, 8H), 3.66 (s, 4H), 3.60 (s, 2H), 3.42 (s, 2H), 2.72–2.67 (m, 2H), 2.50–2.45 (m, 2H), 2.33 (s, 3H), 2.03 (s, 6H); ¹³C NMR: δ 157.17, 156.96, 145.83, 145.78, 139.29, 137.91, 137.80, 133.45, 133.30, 128.98, 127.85, 126.62, 122.28, 122.22, 59.99, 58.83, 51.92, 51.54, 18.40, 17.95.

Synthesis of N-hydroxyethyl-N,N',N'-tris(3-methylpyridin-2-ylmethyl)ethylene-1,2-diamine (L5). This synthesis is performed analogously to the synthesis for L6. Starting from 2-hydroxymethyl-3-methyl pyridine (3.49 g, 28.4 mmol), and N-hydroxyethyl ethylene-1,2-diamine (656 mg 6.30 mmol), after 7 days N-hydroxyethyl-N,N',N'-tris(3-methylpyridin-2-ylmethyl)ethylene-1,2-diamine (L5, 379 mg, 0.97 mmol, 14%) was obtained.

¹H NMR: δ 8.31–8.28 (m, 31H), 7.35–7.33 (m, 3H), 7.06–7.00 (m, 3H), 4.71 (br s, 1H), 3.73 (s, 4H), 3.61 (s, 2H), 3.44 (t, J=5.1, 2H), 2.68 (s, 4H), 2.57 (t, J=5.0, 2H), 2.19 (s, 3H), 2.10 (s, 6H); ¹³C NMR: δ 157.01, 156.88, 145.91, 145.80, 137.90, 137.83, 133.30, 131.89, 122.30, 121.97, 59.60, 59.39, 57.95, 56.67, 51.95, 51.22, 18.14, 17.95.

Synthesis of N-methyl-N,N',N'-tris(5-methylpyridin-2-ylmethyl)ethylene-1,2-diamine (L6). 2-hydroxymethyl-5-methyl pyridine (2.70 g, 21.9 mmol) was dissolved in dichloromethane (25 mL). Thionyl chloride (25 mL) was added dropwise under cooling (ice bath). The resulting mixture was stirred for 1 hour and the solvents removed in vacuo (rotavap, until p=20 mm Hg, T±35° C.). The remaining oil was used directly in the synthesis of the ligands, since it was known from the literature that the free picolyl chlorides are somewhat unstable and are highly lachrymatory. To the resultant mixture was added dichloromethane (25 mL) and N-methyl ethylene-1,2-diamine (360 mg, 4.86 mmol). Subsequently NaOH (5 N, aq.) was added dropwise. The reaction was quite vigorous in the beginning, since part of the thionyl chloride was still present. The aqueous layer was brought to pH=10, and additional NaOH (5 N. 4.38 mL) was added. The reaction mixture was stirred until a sample indicated complete conversion (7 days). The reaction mixture was extracted with dichloromethane (3×25 mL). The combined organic phases were dried and the solvent removed in vacuo. Purification was enforced by column chromatography (aluminium oxide 90 (activity II–III according to Brockmann); triethylamine:ethyl acetate:petroleum ether 40–60=1:9:10) until the impurities were removed according to TLC (aluminium oxide, same eluent, Rf≈0.9). The compound was eluted using ethyl acetate:triethyl amine=9:1, yielding N-methyl-N,N',N'-tris(5-methylpyridin-2-ylmethyl)ethylene-1,2-diamine (L6, 685 mg, 1.76 mmol, 36%) as a slightly yellow oil.

¹H NMR: δ 8.31 (s, 31H) 7.43–7.35 (m, 51H), 7.21 (d, J=7.8, 1H), 3.76 (s, 4H), 3.56 (s, 2H), 2.74–2.69 (m, 2H), 2.63–2.58 (m, 2H), 2.27 (s, 6H), 2.16 (s, 3H); ¹³C NMR: δ 156.83, 156.43, 149.23, 149.18, 136.85, 136.81, 131.02, 122.41, 122.30, 63.83, 60.38, 55.53, 52.00, 42.76, 18.03.

Synthesis of N-methyl-N,N',N'-tris(5-ethylpyridin-2-ylmethyl)ethylene-1,2-diamine (L7). This synthesis is performed analogously to the synthesis for L6. Starting from 2-hydroxymethyl-5-ethyl pyridine (3.00 g, 21.9 mmol), and N-methyl ethylene-1,2-diamine (360 mg, 4.86 mmol), after 7 days N-methyl-N,N',N'-tris(5-ethylpyridin-2-ylmethyl) ethylene-1,2-diamine (L7, 545 mg, 1.26 mmol, 26%) was obtained.

H NMR: δ 8.34 (s, 3H), 7.44–7.39 (m, 5H), 7.26 (d, J=6.6, 1H), 3.80 (s, 4H), 3.59 (s, 2H), 2.77–2.72 (m, 2H), 2.66–2.57 (m, 8H), 2.18 (s, 3H), 1.23 (t, J=7.5, 9H); ¹³C NMR: δ 157.14, 156.70, 148.60, 148.53, 137.25, 135.70, 122.59, 122.43, 63.91, 60.48, 55.65, 52.11, 42.82, 25.73, 15.36.

(ii) Synthesis of Metal-ligand Complexes:

Synthesis of N-methyl-N,N',N'-tris(3-methylpyridin-2-ylmethyl)ethylene-1,2-diamine iron(II)chloride.PF₆ ([L2 Fe(II)Cl]PF₆). FeCl₂.4H₂O (51.2 mg,257 μmol) was dissolved in MeOH:H₂O=1:1 (2.5 mL). The solution was heated to 50° C. Added was N-methyl-N,N',N'-tris(3-methylpyridin-2-ylmethyl)ethylene-1,2-diamine (L2, 100 mg, 257 μmol) in MeOH:H₂O=1:1 (2.0 mL). Subsequently NaPF₆ (86.4 mg, 514 μmol) in H₂O (2.5 mL) was added dropwise. Cooling to room temperature, filtration and drying in vacuo (p=0.05 mm Hg, T=room temperature) yielded the complex [L2 Fe(II)Cl]PF₆ (149 mg, 239 μmol, 93%) as a yellow solid.

¹H NMR(CD₃CN, paramagnetic): δ 167.17, 142.18, 117.01, 113.34, 104.79,98.62, 70.77, 67.04, 66.63, 58.86, 57.56, 54.49, 51.68, 48.56, 45.90, 27.99, 27.36, 22.89, 20.57, 14.79, 12.14, 8.41, 8.16, 7.18, 6.32, 5.78, 5.07, 4.29, 3.82, 3.43, 2.91, 2.05, 1.75, 1.58, 0.94, 0.53, −0.28, −1.25, −4.82, −18.97, −23.46.

Synthesis of N-ethyl-N,N',N'-tris(3-methylpyridin-2-ylmethyl)ethylene-1,2-diamine iron(II)chloride.PF₆ ([L3 Fe(II)Cl]PF₆). This synthesis was performed analogously to the synthesis for [L2 Fe(II)Cl]PF₆. Starting from N-ethyl-N,N',N'-tris(3-methylpyridin-2-ylmethyl)ethylene-1,2-diamine (L3, 104 mg, 257 μmol) gave the complex [L3 Fe(II)Cl]PF₆ (146 mg, 229 μmol, 89%) as a yellow solid.

¹H NMR (CD₃CN, paramagnetic): δ 165.61, 147.20, 119.23, 112.67, 92.92, 63.14, 57.44, 53.20, 50.43, 47.80, 28.59, 27.09, 22.48, 8.55, 7.40, 3.63, 2.95, 2.75, 2.56, 2.26, 1.75, 1.58, 0.92, 0.74, −0.28, −1.68, −2.68, −12.36, −28.75.

Synthesis of N-benzyl-N,N',N'-tris(3-methylpyridin-2-ylmethyl)ethylene-1,2-diamine iron(II)chloride.PF₆ ([L4 Fe(II)Cl]PF₆). This synthesis was performed analogously to the synthesis for [L2 Fe(II)Cl]PF₆. Starting from N-benzyl-N,N',N'-tris(3-methylpyridin-2-ylmethyl)ethylene-1,2-diamine (L4, 119.5 mg, 257 μmol) gave the complex (172 mg, 229 μmol, 95%) as a yellow solid.

¹H NMR (CD₃CN, paramagnetic): δ 166.33, 145.09, 119.80, 109.45, 92.94, 57.59, 52.83, 47.31, 28.40, 27.89, 16.28, 11.05, 8.70, 8.45, 7.69, 6.99, 6.01, 4.12, 2.89, 2.71, 1.93, 1.56, −0.28, −1.68, −2.58, −11.40, 25.32.

Example 4

This example describes a synthesis of a catalyst of formula (H) wherein:

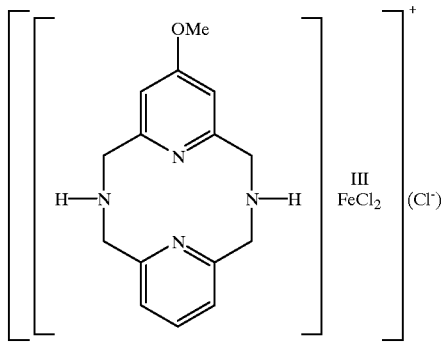

$R_2-R_8=H$; $R_1=4-MeO$; x=1; y=1; z=1; X=Cl, n=2; Y=Cl$^-$, p=1.

(i) Synthesis of the Ligand 2,11-diaza[3.3]-(4-methoxy))(2,6)pyridinophane ((4OMe)LN$_4$H$_2$):

4-chloro-2,6-pyridyl dimethyl ester (2). A mixture of 4-hydroxy-2,6-pyridine dicarboxylic acid (12.2 g, 60 mmoles) and PCl$_5$ (41.8 g, 200 mmoles) in 100 ml of CCl$_4$ was refluxed until the evolution of HCl ceased. Absolute methanol (50ml) was slowly added. After cooling, all the volatile material was removed. The mixture was then poured into 200 ml of water and ice. The diester crystallised immediately and was collected by filtration (70%). $^1$H NMR (200MHz, H$_2$O) δ 7.60 (2H,s), 4.05 (6H, s).

4-methoxy-2,6-pyridine dimethanol (4). Metallic sodium (1 g, 44 mmoles) was dissolved into 200 ml of dry methanol. 4-chloro-2,6-pyridyl dimethyl ester (9.2 g, 40 mmoles) was then added and the mixture was refluxed for 3 hours to obtain pure 4-methoxy-2,6-pyridyl dimethyl ester. To this solution, at RT, NaBH$_4$ (9.1 g, 240 mmoles) was added in small portions and the mixture was refluxed for 16 hours. Acetone (30 ml) was then added and the solution refluxed for an additional 1 hour. After all the volatile material was removed, the residue was heated with 60 ml of a saturated NaHCO$_3$/Na$_2$CO$_3$ solution. After dilution with 80 ml of water, the product was continuously extracted with CHCl$_3$ for 2–3 days. Evaporation of the CHCl$_3$ yielded 83% of 4-methoxy-2,6-pyridine dimethanol. $^1$H NMR (200MHz, H$_2$O) δ 6.83 (2H,s), 5.30 (2H,s), 4.43 (4H,s), 3.82 (3H, s).

4-methoxy-2,6-dichloromethylpyridine (5). This synthesis is carried out according literature.

N,N'-ditosyl-2,11-diaza[3.3]-(4-methoxy)(2,6)pyridinophane. the procedure is similar to that described in the literature. The crude product obtained is practically pure (yield=95%.)

$^1$H-NMR (CDCl$_3$, 250 MHz): 7.72 (4H, d, J=7Hz), 7.4 (1H, t, J=6Hz), 7.35 (4H, d, J=7Hz), 7.1 (1H, d, J=6Hz), 6.57 (2H, s), 4.45 (4H, s), 4.35 (4H, s), 3.65 (3H, s), 2.4 (6H, s).

2,11-diaza[3.3]-(4-methoxy)(2,6)pyridinophane. The procedure is similar to the one described previously. The crude product obtained is purified by chromatography (alumina, CH$_2$Cl$_2$/MeOH 95:5), yield =65%.

$^1$H-NMR (CDCl$_3$, 250 MHz): 7.15 (1H, t, J=6Hz), 6.55 (1H, d, J=6Hz), 6.05 (2H, s), 3.95 (4H, s), 3.87 (4H, s), 3.65 (3H, s). Mass spectrum (EI): M$^+$=270 (100%).

(ii) Synthesis of the Complex [Fe(4OMeLN$_4$H$_2$)Cl$_2$]Cl:

270 mg of 2,11-diaza[3.3]-(4-methoxy)(2,6) pyridinophane (1 mmole) were dissolved in 15 ml of dry THF. To this solution was added a solution of 270 mg of FeCl$_3$.6H$_2$O (1 mmoles) in 5 ml of MeOH. The resulting mixture is evaporated to dryness and the solid product is dissolved in 10 ml of AcN with a minimum of MeOH. Slow diffusion of THF give 300 mg of brown crystals, yield=70%. Elemental analysis for C$_{15}$H$_{18}$N$_4$Cl$_3$OFe.0,5MeOH (found/theoretical): C=41.5/41.61 H=4.46/4.52 N=12.5/12.08.

IR (KBr pellets, cm$^{-1}$): 3545, 3414, 3235, 3075, 2883, 1615. 1477, 1437, 1340,1157, 1049,883,628,338.

Example 5

This example describes a synthesis of a catalyst of formula (H) wherein:

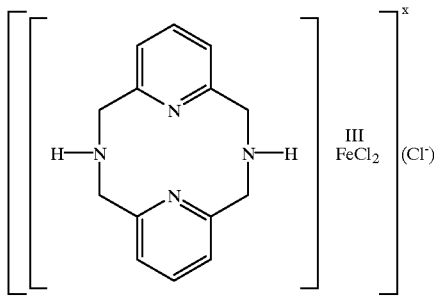

$R_1-R_8=H$; x=1; y=1; z=1; X=Cl, n=2; Y=Cl$^-$, p=1

Synthesis of the Complex [Fe(LN$_4$H$_2$)Cl$_2$]Cl:

240 mg of LN$_4$H$_2$ (1I mmoles) were dissolved in 15 ml of dry THF. To this solution was added a solution of 270 mg of FeCl$_3$.6H$_2$O (1 mmole) in 5 ml of MeOH. The resulting mixture is stirred and gives spontaneously 340 mg of yellow powder, yield=85%. IR (KBr pellets, cm$^{-1}$): 3445, 3031, 2851, 1629, 1062, 1473, 1427, 1335, 1157,1118, 1045,936, 796,340,318.

Example 6

This Example describes a synthesis of a catalyst of formula (H) wherein:

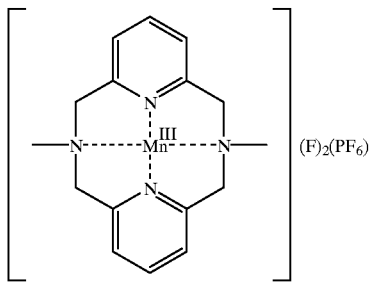

$R_1=R_2=R_{5-8}=H$; $R_3=R_4=Me$; x=1; y=1; n=2; z=1; X=F$^-$; m=2; Y=PF$^-_6$; p=1 difluoro[N,N'dimethyl-2,11-diaza[3.3](2,6) pyridinophane]maneanese(III) hexafluorophosphate.

(i) Synthesis of the Liand N,N'dimethyl-2,11-diaza[3.3](2.6) pyridinophane:

2,6-dichloromethylpyridine. A mixture of 2,6-dimethanolpyridine (5g, 36 mmoles) and 75 ml of SOCl$_2$ was refluxed for 4 hours. The mixture was concentrated (half volume). Toluene was added (50 ml). The solid formed after cooling was then filtered and dissolved in water and the solution neutralised with NaHCO$_3$. The solid obtained is filtered and dried (65%). $^1$H NMR (200 MHz, CDCl$_3$) δ 7.8 (1H,t, J=7Hz), 7.45 (2H,d, J=7 Hz), 4.7 (4H, s).

Sodium p-toluenesulphonamidure. To a mixture of Na° in dry EtOH (0.7 g, 29 mmoles) was added p-toluenesulphonamide (5 g, 29 mmoles) and the solution was refluxed for 2 hours. After cooling, the solid obtained was filtered, washed with EtOH and dried (quantitative yield).

N,N'-ditosyl-2,11-diaza[3.3](2.6)pyridinophane. To a solution of sodium p-toluenesulphonamidure (1.93 g, 10 mmoles) in 200 ml of dry DMF at 80° C. was slowly added 2,6-dichloromethylpyridine (1.76 g, 10 mmoles). After 1 hour a new portion of sodium p-toluenesulphonamidure was added (1.93 g) and the final mixture stirred at 80° C. for an addition 4 hours. The solution was then evaporated to dryness. The solid obtained was washed with water and then with EtOH and finally crystallised in an $CHCl_3$/MeOH mixture. The solid obtained is filtered and dried. The yield of (15) was 55%. $^1$H NMR (200 MHz, $CDCl_3$) δ 7.78 (4H, d, J=6Hz), 7.45 (6Hm), 7.15 (4H,d, J=6Hz), 4.4 (8H, s), 2.4 (6H,s)

2,11-diaza[3.3](2,6)pyridinophane. A mixture of N,N'-ditosyl-2,11-diaza[3.3](2,6)pyridinophane (1.53 g, 2.8 mmoles) and 14 ml of $H_2SO_4$ 90% was heated at 110° C. for 2 hours. The solution, cooled and diluted with 14 ml of water, was then carefully poured into a saturated NaOH solution. The solid formed is extracted with chloroform. The organic layer is evaporated to dryness to yield 85% of 2,11 -diaza[3.3](2,6)pyridinophane. $^1$H NMR (200 MHz, $CDCl_3$) δ 7.1 (2H,t, J=7Hz), 6.5 (4H,d, J=7 Hz), 3.9 (8H, s).

N,N'-dimethyl-2,11-diaza[3.3](2,6)pyridinophane. A mixture of 2,11-diaza[3.3](2,6)pyridinophane (0.57 g, 2.4 mmoles), 120 ml of formic acid and 32 ml of formaldehyde (32% in water) was refluxed for 24 hours. Concentrated HCl (10 ml) were added and the solution evaporated to dryness. The solid was dissolved in water and basified with NaOH 5M, and the resulting solution was extracted with $CHCl_3$. The solid obtained was purified by chromatography on alox ($CH_2Cl_2$+1% MeOH) to yield 51% of N,N'-dimethyl-2,11-diaza[3.3](2,6)pyridinophane. $^1$H NMR (200 MHz, $CDCl_3$) δ 7.15 (2H,t, J=7Hz), 6.8 (4H,d, J=7 Hz), 3.9 (8H, s), 2.73 (6H,s).

(ii) Synthesis of the Complex:

$MnF_3$ (41.8 mg, 373 mmoles) was dissolved in 5 ml of MeOH, and N,N'-dimethyl-2,11-diaza[3.3](2,6)pyridinophane (0.1 g, 373 mmoles) was added with 5 ml of THF. After 30 minutes of stirring at RT, 4 ml of THF saturated in $NBu_4PF_6$ were added, and the solution left without stirring until the crystallisation was finished. The product was collected by filtration to yield 80% of complex. Elemental analysis (found, theoretical): % C (38.35, 37.94), % N (11.32, 11.1), % H (3.75, 3.95). IR (KBr pellet, $cm^{-1}$): 3086, 2965, 2930, 2821, 1607, 1478, 1444, 1425, 1174, 1034, 1019, 844, 796, 603, 574, 555. UV-Vis ($CH_3CN$, λ in nm, ε): 500, 110; 850, 30; ($CH_3CN/H_2O$:1/1, λ in nm, ε): 465, 168; 850, 30.

Example 7

Bleaching of Tomato-oil Stained Cloths Without and With Addition of [Fe(MeN4Py)($CH_3CN$)]($ClO_4$)$_2$, Immediately After the Wash (t=0) and After 24 h Storage (t=1 day).

In an aqueous solution containing 10 mM carbonate buffer (pH 10) without and with 0.6 g/l LAS (linear alkylbenzene sulphonate) or containing 10 mM borate buffer (pH 8) without and with 0.6 g/l LAS, tomato-soya oil stained cloths (6×6 cm) were added and stirred for 30 minutes at 30° C. In a second series of experiments, the same tests were done in the presence of 10 μM [Fe(MeN4Py)($CH_3CN$)]($ClO_4$)$_2$, referred to in the table below as Fe(MeN4Py).

After the wash, the cloths were dried in a tumble drier and the reflectance was measured with a Minolta 3700d spectrophotometer at 460 nm. The difference in reflectance before and after the wash is defined as ΔR460 value.

The cloths were measured immediately after the wash (t=0), and after 24 h storage in a dark room under ambient conditions (t=1d). The results obtained are listed in the table below:

|  | ΔR value (t = 0) blank (no cat) | ΔR value (t = 0) +Fe(MeN4Py) | ΔR value (t = 1d) blank | ΔR value (t = 1d) +Fe(MeN4Py) |
|---|---|---|---|---|
| pH 8 no LAS | 11.5 | 23 | 11.5 | 44 |
| pH 8 with LAS | 12.5 | 19 | 12.5 | 36 |
| pH 10 no LAS | 10.5 | 30 | 11.5 | 43 |
| pH 10 with LAS | 12.5 | 30 | 14 | 39 |

Example 8

Bleaching of Tomato-oil Stained Cloths Without and With Addition of Various Metal Catalysts Measured Immediately After Drying.

In an aqueous solution containing 10 mM carbonate buffer (pH 10) without and with 0.6 g/l LAS (linear alkylbenzene sulphonate) or containing 10 mM borate buffer (pH 8) without and with 0.6 g/l LAS, tomato-soya oil stained cloths were added and kept in contact with the solution under agitation for 30 minutes at 30° C. In comparative experiments, the same experiments were done by addition of 5 μM of dinuclear or 10 μM mononuclear complex, referred to in the table below.

After the wash, the cloths were rinsed with water and subsequently dried at 30° C. and the change in colour was measured immediately after drying with a Linotype-Hell scanner (ex Linotype). The change in colour (including bleaching) is expressed as the ΔE value. The measured colour difference (ΔE) between the washed cloth and the unwashed cloth is defined as follows:

$$\Delta E=[(\Delta L)^2+(\Delta a)^2+(\Delta b)^2]^{1/2}$$

wherein ΔL is a measure for the difference in darkness between the washed and unwashed test cloth; Δa and Δb are measures for the difference in redness and yellowness respectively between both cloths. With regard to this colour measurement technique, reference is made to Commission International de l'Eclairage (CIE); Recommendation on Uniform Colour Spaces, colour difference equations, psychometric colour terms, supplement no 2 to CIE Publication, no 15, Colormnetry, Bureau Central de 1a CIE, Paris 1978.

The following complexes were used:
i) [$Mn_2$(1,4,7-trimethyl-1,4,7-triazacyclononane)$_2$(μ-O)$_3$] ($PF_6$)$_2$(1) Synthesised according to EP-B-458397;
ii) [Mn(LN4Me2)] (=difluoro[N,N'dimethyl-2,11-diaza [3.3](2,6)pyridinophane] manganese(III) hexafluorophosphate) (2)
Synthesised as described previously;
iii) [Fe(OMe)LN4H2)$Cl_2$] (=Fe(2,11-diaza[3.3]-(4-methoxy)(2,6)pyridinophane)$Cl_2$ (3)
Synthesised as described previously;
iv) C12-CoCo (4)
Synthesised according to EP-A-408131;
v) Me2CoCo (5)
Synthesised according to EP-A-408131;
vi) [Fe(tpen)]($ClO_4$)$_2$ (6)
Synthesised according to WO-A-9748787;

vii) [Fe(N,N,N'-tris(pyridin-2ylmethyl)-N-methyl-1,2-ethylenediamine)Cl](PF$_6$)$_2$ (7)
  Synthesised according to I. Bernal, et al., *J. Chem. Soc., Dalton Trans*, 22, 3667 (1995);

viii) [Fe$_2$(N,N,N'N'-tetrakis(benzimidazol-2-ylmethyl)-propan-2-ol-1,3-diamine)($\mu$-OH)(NO$_3$)$_2$](NO$_3$)$_2$ (8)
  Synthesised according to Brennan, et al., *Inorg. Chem.*, 30, 1937 (1991);

ix) [Mn$_2$(tpen)($\mu$-O)$_2$($\mu$-OAc)](ClO$_4$)$_2$ (9)
  Synthesised according to Tofilund, H.; Markiewicz, A.; Murray, K. S.; *Acta Chem. Scamd.*, 44, 443 (1990);

x) [Mn(N,N,N'-tris(pyridin-2-ylmethyl)-N'-methyl-1,2-ethylenediamine)Cl](PF$_6$) (10)
  Synthesised as follows:
  To a solution of manganese chloride tetrahydrate in tetrahydrofuran (0. 190 g, 1 mmol of MnCl$_2$.4H$_2$O in 10 mL of THF) ligand trispicen(NMe) (0.347, 1 mmol) was added to give a brown precipitate (reference ligand: I. Bernal, et al., *J. Chem. Soc., Dalton Trans*, 22, 3667 (1995)). The mixture was stirred for 10 minutes and ammonium hexafluorophosphate (0.163 g, 1 mmol) dissolved in THF was added to give a cream coloured precipitate. The mixture was filtered, the filtrate was washed with THF and dried under vacuum to furnish the complex (FW=522.21 g.mol$^{-1}$) as a white solid (0.499 g, 86%). ESMS (m/z): 437 ([LMnCl]$^+$)

xi) [Mn$_2$(N,N'-bis(pyridin-2-ylmethyl)-1,2-ethylenediamine)$_2$($\mu$-O)$_2$](ClO$_4$)$_3$ (11)
  Synthesised according to Glerup, J.; Goodson, P. A.; Hazell, A.; Hazell, R.; Hodgson, D. J.; McKenzie, C. J.; Michelsen, K.; Rychlewska, U.; Toftlund, H. *Inorg. Chem.* (1994), 33(18), 4105–11;

xii) [Mn(N,N'-bis(pyridin-2-ylmethyl)-N,N'-dimethyl-1,2-ethylenediamine)$_2$Cl$_2$] (12)
  Synthesised as follows:
  Triethylamine (0.405 g, 4 mmol) was a solution of salt of the ligand bispicen(NMe) (0.416 g, 1 mmol) in tetrahydrofuran anhydrous (10 mL) (ref ligand: C. Li, et al, J. Chem. Soc., Dalton Trans. (1991), 1909–14). The mixture was stirred at room temperature for 30 minutes. A few drops of methanol were added. The mixture was filtered. Manganese chloride (0.198 g, 1 mmol) dissolved in THF (1 mL) was added to the mixture to give, after a stirring of 30 minutes, a white precipitate. The solution was filtered, the filtrate was washed twice with dry ether and dried under vacuum. This gave 0.093 g of complex (23% yield).

xiii) [Mn$_2$(N,N,N'N'-tetrakis(pyridin-2-ylmethyl)-propan-1,3-diamine)($\mu$-O)($\mu$-OAc)$_2$](ClO$_4$)$_2$ (13)
  Synthesised as follows:
  To a stirred solution of 6.56 g 2-chloro-methylpyridine (40 mmol) and 0.75 ml 1,3-propanediamine (9 mmol) in 40 ml water, is added slowly at 70° C. over a period of 10 minutes, 8 ml 10 M NaOH-solution. The colour of the reaction turned from yellow to deep red. The reaction was stirred for an additional 30 minutes at 70° C., after which the reaction was cooled to room temperature. The reaction mixture was extracted with dichloromethane (totally 200 ml), after which the red organic layer was dried over MgSO$_4$, filtered and evaporated under reduced pressure, to yield 4.51 g of a red/brown oil. After scratching the bottom with a spatula the residue turned solid, trying to purify the crude product by washing it with water the product became messy, so immediately the purification was stopped and dried with ether. A sample was taken to analyse the product by NMR, while the rest was immediately reacted with Mn(OAc)$_3$ (see complexation).
  $^1$H-NMR (400 MHz) (CDCl$_3$); d (ppm): 1.65 (q-5, propane-A, 2H), 2.40 (t, propane-B, 4H), 3.60 (s, N—CH$_2$-pyr, 8H), 6.95 (t, pyr-H4, 4H), 7.30 (d, pyr-H3, 4H), 7.45 (t, pyr-H5, 4H), 8.35 (d, pyr-H6, 4H).
  To a stirred solution of 4.51 g TPTN (0.0103 mol) in 40 ml methanol is added at room temperature (22° C.) 2.76 g Mn(OAc)$_3$ (0.0103 mol). The colour of the reaction turned from orange to dark brown, after the addition the mixture was stirred for 30 minutes at room temperature and filtered. To the filtrate was added at room temperature 1.44 g NaClO$_4$ (0.0103 mmol) and the reaction mixture was stirred for another hour, filtered and nitrogen dried, yielding 0.73 g bright brown crystals (8%).
  $^1$H-NMR (400 MHz) (CD$_3$CN); d (ppm): -42.66 (s), -15.43 (s), -4.8 (s, br.), 0–10 (m, br.), 13.81 (s), 45.82 (s), 49.28 (s), 60 (s, br.), 79 (s, br.), 96 (s, br.) IR/(cm$^{-1}$): 3426, 1608 (C=C), 1563 (C=N), 1487 , 1430 (C—H), 1090 (ClO$_4$), 1030, 767,623. UV/Vis ($\lambda$, nm($\epsilon$, 1·mol$^{-1}$·cm$^{-1}$): 260 (2.4×10$^4$), 290 (sh), 370 (sh), 490 (5.1×10$^2$), 530 (sh; 3.4×10$^2$), 567 (sh), 715 (1.4×10$^2$). Mass spectrum: (ESP+) m/z 782 [TPTN Mn(II)Mn(III)($\mu$-OH)($\mu$-OAc)$_2$ (ClO$_4$)$^{-1+}$; ESR (CH$_3$CN): The complex is ESR silent supporting the presence of a Mn(III)Mn(III) species. Elemental analysis: found (expected for Mn$_2$C$_{31}$H$_{38}$N$_6$O$_{14}$Cl$_2$ (MW=899): C 41.14 (41.4), H 4.1 (4.2), N 9.23 (9.34), O 24.8 (24.9), Cl 7.72 (7.9), Mn 12.1 (12.2).

xiv) [Mn$_2$(tPa)$_2$($\mu$-O)$_2$](PF$_6$)$_3$ (14)
  Synthesised according to D. K. Tovile, C. A. Botsford, D. J. Hodgson, ICA, 141, 167 (1988);

xv) [Fe(N4Py)(CH$_3$CN)](ClO$_4$)$_2$ (15)
  Synthesised according to WO-A-9534628;

xvi) [Fe(MeN4Py)(CH$_3$CN)](ClO$_4$)$_2$ (16)
  Synthesised according to EP-A-0909809.

Results:

TABLE bleach activity on Tomato Oil stains expressed in ΔE values obtained for various metal complexes.

| | BL * | 1 | 2 | 3 | 4 | 5 | 6 | 7 | 8 | 9 | 10 | 11 | 12 | 13 | 14 | 15 | 16 | 16 ** |
|---|---|---|---|---|---|---|---|---|---|---|---|---|---|---|---|---|---|---|
| pH 8 -LAS | 1 | 1 | 2 | 2 | 2 | 2 | 1 | 6 | 2 | 1 | 5 | 2 | 2 | 1 | 4 | 17 | 16 | 3 |
| pH 8 +LAS | 2 | 4 | 4 | 4 | 2 | 3 | 18 | 17 | 2 | 15 | 6 | 10 | 5 | 4 | 5 | 15 | 18 | 21 |

TABLE-continued bleach activity on Tomato Oil stains expressed in ΔE values obtained for various metal complexes.

| | BL* | 1 | 2 | 3 | 4 | 5 | 6 | 7 | 8 | 9 | 10 | 11 | 12 | 13 | 14 | 15 | 16 | 16** |
|---|---|---|---|---|---|---|---|---|---|---|---|---|---|---|---|---|---|---|
| pH 10 −LAS | 1 | 1 | 1 | 1 | 5 | 10 | 1 | 3 | 4 | 1 | 1 | 2 | 2 | 2 | 1 | 11 | 17 | 6 |
| ph 10 +LAS | 3 | 7 | 7 | 5 | 4 | 5 | 5 | 8 | 4 | 3 | 3 | 7 | 10 | 3 | 4 | 14 | 18 | 16 |

\* BL: Reference: no catalyst added, only buffer with and without LAS
\** Compound 16 with 10 mM hydrogen peroxide

What is claimed is:

1. A bleaching composition comprising, in an aqueous medium, atmospheric oxygen and a complex having the formula $[Fe(MeN4Py)(CH_3CN)](ClO_4)_2$, wherein (MeN4Py) is N,N-bis(pyridin-2-yl-methyl)-1,1-bis(pyridin-2-yl)-1-aminoethane, the complex catalysing bleaching of a substrate by the atmospheric oxygen, wherein the aqueous medium is substantially devoid of peroxygen bleach or a peroxy-based or -generating bleach system.

2. A bleaching composition according to claim 1, wherein the medium has a pH value in the range from pH 6 to 11.

3. A bleaching composition according to claim 2, wherein the medium has a pH value in the range from pH 8 to 10.

4. A bleaching composition according to claim 1, wherein the medium is devoid of a transition metal sequestrant.

5. A bleaching composition according to claim 1, wherein the medium further comprises a surfactant.

6. A bleaching composition according to claim 1, wherein the medium further comprises a builder.

* * * * *